United States Patent
Ghosh et al.

(10) Patent No.: US 10,780,281 B2
(45) Date of Patent: Sep. 22, 2020

(54) EVALUATION OF VENTRICLE FROM ATRIUM PACING THERAPY

(71) Applicant: Medtronic, Inc., Minneapolis, MN (US)

(72) Inventors: Subham Ghosh, Blaine, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 406 days.

(21) Appl. No.: 15/934,517

(22) Filed: Mar. 23, 2018

(65) Prior Publication Data

US 2019/0290909 A1 Sep. 26, 2019

(51) Int. Cl.
| | | |
|---|---|---|
| A61N 1/368 | (2006.01) | |
| A61B 5/0408 | (2006.01) | |
| A61N 1/365 | (2006.01) | |
| A61N 1/37 | (2006.01) | |
| A61N 1/362 | (2006.01) | |
| A61N 1/04 | (2006.01) | |
| A61B 5/04 | (2006.01) | |
| A61B 5/00 | (2006.01) | |
| A61B 5/0456 | (2006.01) | |
| A61B 5/0464 | (2006.01) | |
| A61B 5/0472 | (2006.01) | |

(52) U.S. Cl.
CPC .............. *A61N 1/3684* (2013.01); *A61B 5/04* (2013.01); *A61B 5/04085* (2013.01); *A61B 5/6805* (2013.01); *A61N 1/0476* (2013.01); *A61N 1/0484* (2013.01); *A61N 1/3624* (2013.01); *A61N 1/3625* (2013.01); *A61N 1/36514* (2013.01); *A61N 1/3702* (2013.01); *A61N 1/3706* (2013.01); *A61B 5/04011* (2013.01); *A61B 5/0456* (2013.01); *A61B 5/0464* (2013.01); *A61B 5/0472* (2013.01); *A61B 5/04087* (2013.01)

(58) Field of Classification Search
CPC .................................................... A61N 1/3684
See application file for complete search history.

(56) References Cited

U.S. PATENT DOCUMENTS

| | | | |
|---|---|---|---|
| 4,233,987 | A | 11/1980 | Feingold |
| 4,402,323 | A | 9/1983 | White |
| 4,428,378 | A | 1/1984 | Anderson et al. |
| 4,497,326 | A | 2/1985 | Curry |
| 4,566,456 | A | 1/1986 | Koning et al. |

(Continued)

FOREIGN PATENT DOCUMENTS

| | | |
|---|---|---|
| CN | 1043621 A | 7/1990 |
| CN | 1253761 A | 5/2000 |

(Continued)

OTHER PUBLICATIONS

International Search Report and Written Opinion dated May 3, 2012 for International Application No. PCT/US2012/036262; 9 pages.

(Continued)

*Primary Examiner* — Alyssa M Alter

(57) ABSTRACT

Cardiac electrical heterogeneity information may be used to determine whether one or more ventricle from atrium (VfA) paced settings for VfA pacing therapy are acceptable. Cardiac electrical heterogeneity information may be generated during VfA pacing, and then evaluated to determine whether the VfA paced settings are acceptable.

27 Claims, 13 Drawing Sheets

(56) References Cited

U.S. PATENT DOCUMENTS

| | | |
|---|---|---|
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,119,959 B2 | 9/2015 | Rys et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |

(56) References Cited

U.S. PATENT DOCUMENTS

| | | |
|---|---|---|
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Ghosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |

(56) References Cited

U.S. PATENT DOCUMENTS

| | | |
|---|---|---|
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0059002 A1 | 3/2016 | Grubac et al. |
| 2016/0184590 A1 | 6/2016 | Ghosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.

(56) References Cited

OTHER PUBLICATIONS

Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4): 376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9): 1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010; pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010;121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," Annals of Biomedical Engineering, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

(56) References Cited

OTHER PUBLICATIONS

International Search Report and Written Opinion dated May 27, 2019 for International Application No. PCT/US2019/023549; 15 pages.

552 — Monitor electrical activity using the plurality of external electrodes

554 — Generate baseline electrical heterogeneity information (EHI)

556 — Generate paced EHI during delivery of ventricle from atrium pacing therapy

558 — Compare the baseline EHI to the paced EHI

560 — Determine whether a paced setting for the ventricle from atrium pacing therapy is acceptable based on the comparison

562 — Adjust the paced setting for the ventricle from atrium pacing therapy

EVALUATION OF VENTRICLE FROM ATRIUM PACING THERAPY

The disclosure herein relates to systems and methods for use in the evaluation of ventricle from atrium (VfA) pacing therapy.

SUMMARY

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). The cardiac therapy can be a ventricle from atrium (VfA) cardiac therapy, including single or multiple chamber pacing (e.g., dual or triple chamber pacing), atrioventricular synchronous pacing, asynchronous pacing, triggered pacing, cardiac resynchronization pacing, or tachycardia-related therapy. In one or more embodiments, the systems, methods, and interfaces may be described as being noninvasive. For example, in some embodiments, the systems, methods, and interfaces may not need, or include, implantable devices such as leads, probes, sensors, catheters, implantable electrodes, etc. to monitor, or acquire, a plurality of cardiac signals from tissue of the patient for use in evaluating the patient and/or cardiac therapy. Instead, the systems, methods, and interfaces may use electrical measurements taken noninvasively using, e.g., a plurality of external electrodes attached to the skin of a patient about the patient's torso.

In at least one embodiment, the exemplary systems and methods can include monitoring electrical activity of a patient to determine electrical heterogeneity information associated with the patient's cardiac activity. The electrical heterogeneity information can be used to determine whether a paced setting is acceptable for delivering ventricle from atrium (VfA) pacing therapy. In response to the paced setting being unacceptable, additional monitoring and determinations of electrical heterogeneity information can be performed using a variety of paced settings in order to determine which of the paced settings are acceptable.

One exemplary system may include an electrode apparatus. The electrode apparatus can include a plurality of external electrodes to monitor electrical activity from tissue of a patient. The exemplary system can further include a computing apparatus. The computing apparatus can include processing circuitry and can be coupled to the electrode apparatus. The computing apparatus can be configured to monitor electrical activity using the plurality of external electrodes. The computing apparatus can be further configured to generate paced (e.g., ventricle from atrium pacing) electrical heterogeneity information based on the monitored electrical activity during delivery of VfA pacing therapy at one or more VfA paced settings. The paced electrical heterogeneity information can be representative of at least one of mechanical cardiac functionality and electrical cardiac functionality. The computing apparatus can be further configured to determine whether one or more of the VfA paced settings for the VfA pacing therapy are acceptable based on the electrical heterogeneity information.

In at least one embodiment, an exemplary method can include monitoring electrical activity from tissue of a patient using a plurality of external electrodes. The method can further include generating paced electrical heterogeneity information based on the monitored electrical activity during delivery of VfA pacing therapy at one or more VfA paced settings. The paced electrical heterogeneity information can be representative of at least one of mechanical cardiac functionality and electrical cardiac functionality. The method can further include determining whether the one or more VfA paced settings associated with the pacing therapy are acceptable based on the paced electrical heterogeneity information.

In at least one embodiment, an exemplary system can include an electrode apparatus. The electrode apparatus can include a plurality of external electrodes to monitor electrical activity from tissue of a patient. The exemplary system can include computing apparatus. The computing apparatus can include processing circuitry and can be coupled to the electrode apparatus. The computing apparatus can be configured to monitor electrical activity using the plurality of external electrodes during delivery of VfA pacing therapy and to generate electrical heterogeneity information during delivery of VfA pacing therapy. The computing apparatus can be further configured to determine whether a VfA paced setting for the VfA pacing therapy is acceptable based on the electrical heterogeneity information generated from the electrical activity using the VfA paced setting and to adjust the paced setting for the VfA pacing therapy based on whether the VfA pacing therapy is acceptable.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIG. 5 is a block diagram of another exemplary method of evaluation of ventricle from atrium pacing therapy.

DETAILED DESCRIPTION OF EXEMPLARY EMBODIMENTS

Figure 1:
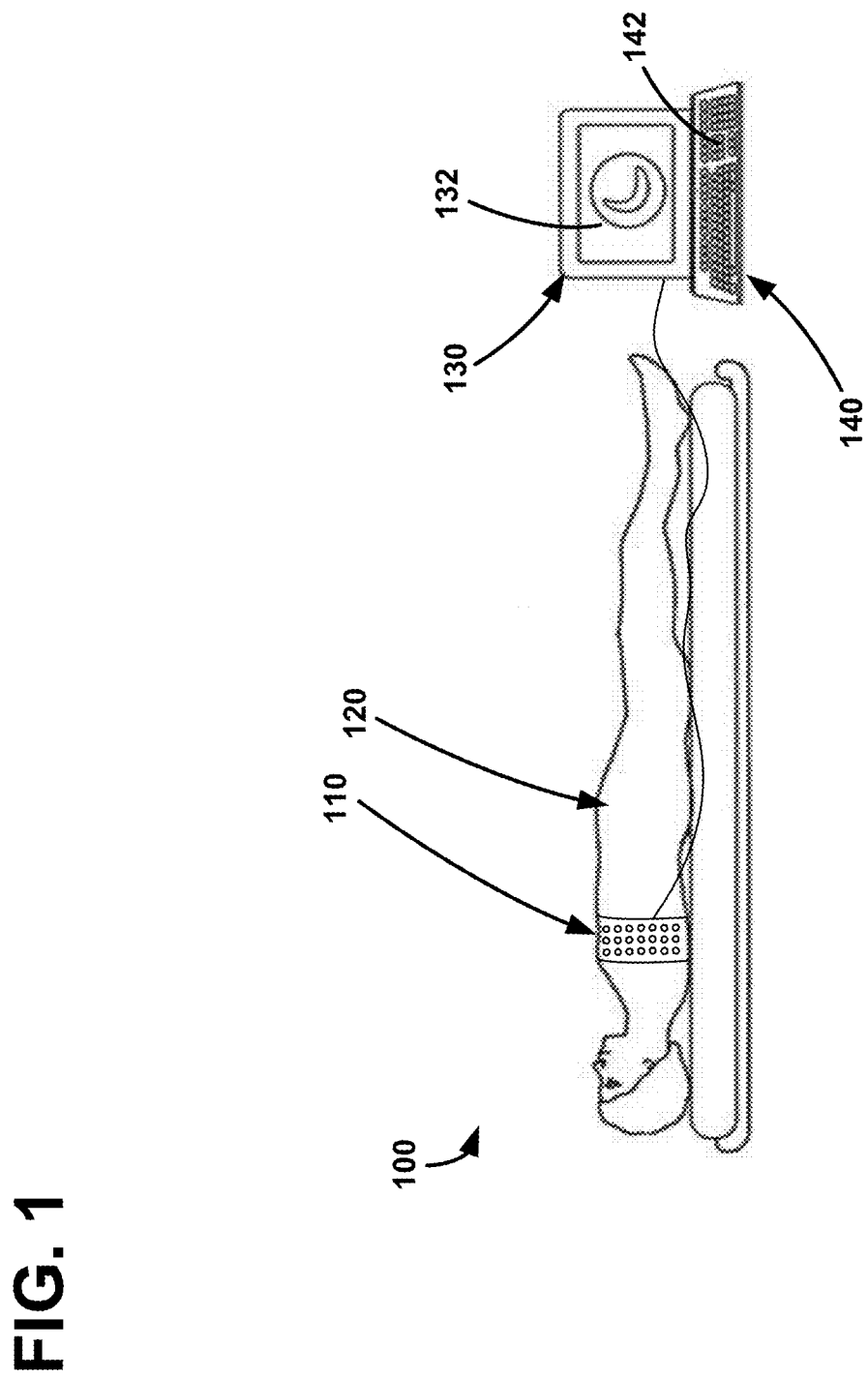
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-13. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Cardiac electrical heterogeneity information can be detected or estimated in proximity of a reference location (e.g., which can be a chosen location for implantation of a pacing lead or leadless device for ventricle from atrium pacing cardiac therapy) using unipolar electrocardiogram (ECG) recordings. Such electrical heterogeneity information may be measured and displayed, or conveyed, to an implanter by a system which acquires the ECG signals and generates various metrics of electrical heterogeneity, such as activation times (e.g., depolarization) measured from various ECG locations.

Various exemplary systems, methods, and interfaces described herein may be configured to use electrode apparatus including external electrodes, display apparatus, and computing apparatus to noninvasively assist a user (e.g., a physician) in the evaluation of a patient's condition and/or ventricle from atrium (VfA) pacing cardiac therapy being performed on, or delivered to, a patient. The VfA pacing cardiac therapy can include pacing a left ventricle of a heart of a patient through an atrium of the heart. A leadless device or pacing lead can be extended (e.g., screwed) through the posterior basal right atrium (a location which can be described as close or in near proximity to the coronary sinus (CS) ostium). The leadless device or pacing lead can be implantable from the triangle of Koch region of the right atrium through the right atrial endocardium and central fibrous body to at least one of deliver cardiac therapy to and sense electrical activity of the left ventricle in the basal and/or septal region of the left ventricular myocardium of a patient's heart. In this way, as an example, a leadless pacing device (e.g., including delivering an appropriate fixation mechanism) may be thus able to sense both atrial activity as well as ventricular activity in addition to atrial-ventricular (AV) synchronous pacing. Further, this VfA pacing therapy may be used for left ventricular (LV) resynchronization for heart failure patients with a left bundle branch block (LBBB). In this case, the VfA pacing therapy may enable easier access to left ventricular endocardium without exposing the leadless pacing device or pacing lead to endocardial blood pool. At the same time, the VfA pacing therapy can help engage part of the conduction system of the heart to potentially correct LBBB and more effectively resynchronize the patient's heart.

The present disclosure can include an implantable medical device including a tissue-piercing electrode and optionally a right atrial electrode and/or a right atrial motion detector. The tissue-piercing electrode may be implanted in the basal and/or septal region of the left ventricular myocardium of the patient's heart from the triangle of Koch region of the right atrium through the right atrial endocardium and central fibrous body. In a leadless implantable medical device, the tissue-piercing electrode may leadlessly extend from a distal end region of a housing of the device, and the right atrial electrode may be leadlessly coupled to the housing (e.g., part of or positioned on the exterior of). The right atrial motion detector may be within the implantable medical device. In a leaded implantable medical device, one or more of the electrodes may be coupled to the housing using an implantable lead. When the device is implanted, the electrodes may be used to sense electrical activity in one or more atria and/or ventricles of a patient's heart. The motion detector may be used to sense mechanical activity in one or more atria and/or ventricles of the patient's heart. In particular, the activity of the right atrium and the left ventricle may be monitored and, optionally, the activity of the right ventricle may be monitored. The electrodes may be used to deliver cardiac therapy, such as single- or multi-chamber pacing for atrial fibrillation, atrioventricular synchronous pacing for bradycardia, asynchronous pacing, triggered pacing, cardiac resynchronization pacing for ventricular dyssynchrony, anti-tachycardia pacing, or shock therapy. Shock therapy may be initiated by the implantable medical device. A separate medical device, such as an extravascular ICD, which may also be implanted, may be in operative communication with the implantable medical device and may deliver an electrical shock in response to a trigger, such as a signaling pulse (e.g., triggering, signaling, or distinctive electrical pulse) provided by the device.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

An exemplary system 100 including electrode apparatus 110, display apparatus 130, and computing apparatus 140 is depicted in FIG. 1. The electrode apparatus 110 as shown includes a plurality of electrodes incorporated, or included, within a band wrapped around the chest, or torso, of a patient 120. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate and position a device to deliver VfA cardiac pacing therapy and/or to locate or select a pacing electrode or pacing vector proximate the patient's heart for Ventricle from atrium pacing therapy in conjunction with the evaluation of Ventricle from atrium pacing therapy.

For example, the exemplary systems, methods, and interfaces may provide image guided navigation that may be used to navigate leads including leadless devices, electrodes, leadless electrodes, wireless electrodes, catheters, etc., within the patient's body while also providing noninvasive cardiac therapy evaluation including determining whether a ventricle from atrium (VfA) paced setting is acceptable or determining whether one or more selected parameters are acceptable, such as selected location information (e.g., location information for the electrodes to target a particular location in the left ventricle). Exemplary systems and methods that use imaging apparatus and/or electrode apparatus may be described in U.S. Patent Publication No. 2014/0371832 filed on Jun. 12, 2013 and entitled "Implantable Electrode Location Selection," U.S. Patent Publication No. 2014/0371833 filed on Jun. 12, 2013 and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical Electrical Vectors," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as locations within the left ventricle, including a selected location within the high posterior basal and/or septal area of the left ventricular cavity) within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in targeting placement of a pacing device and/or evaluating pacing therapy at that location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of a leadless pacing device being positioned or placed to provide VfA pacing therapy, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
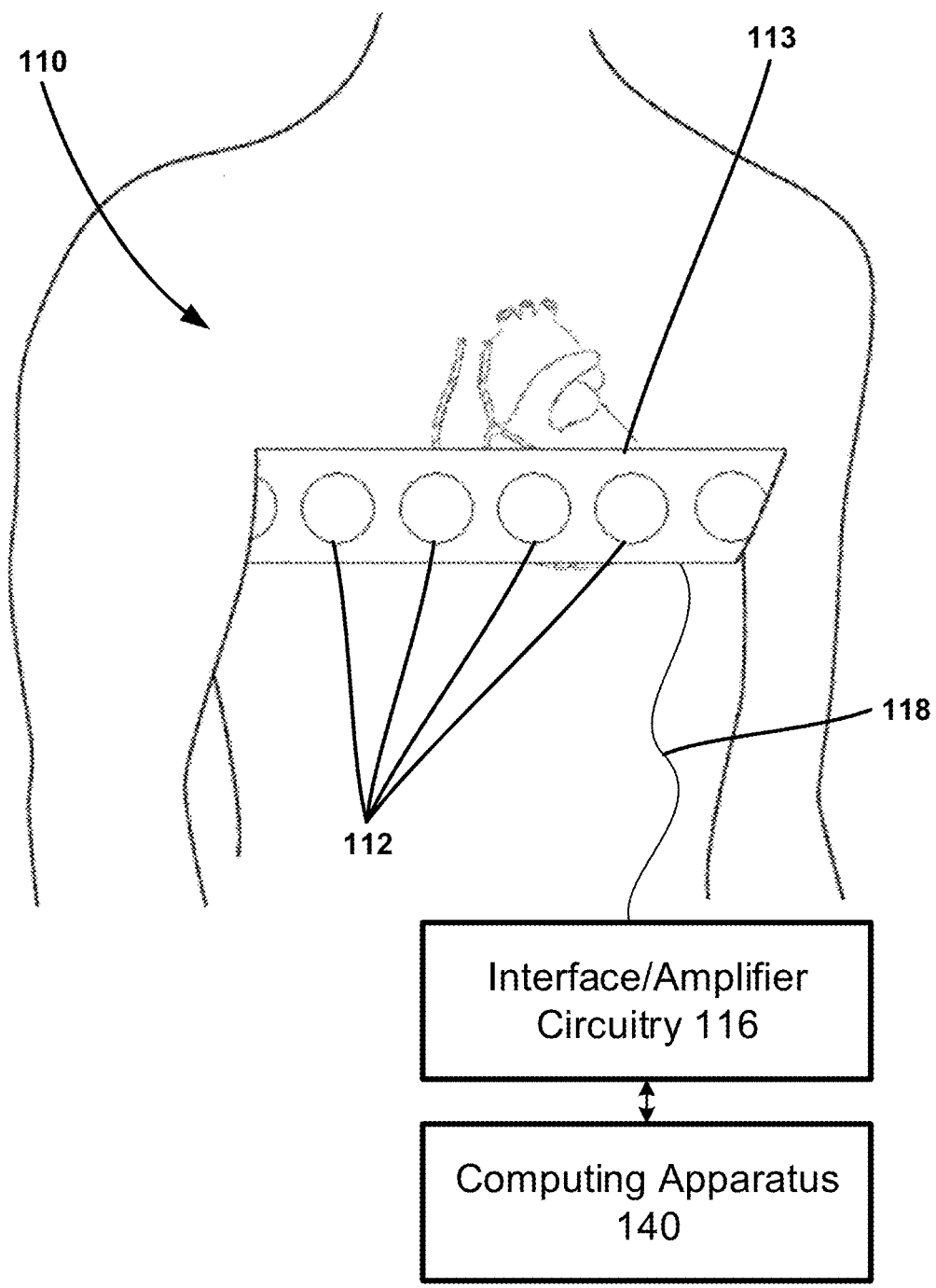
FIGS. 2-3 are diagrams of exemplary external electrode apparatus for measuring torso-surface potentials.

Electrical activation times of the patient's heart may be useful to evaluate a patient's cardiac condition and/or ventricle from atrium (VfA) cardiac therapy being delivered to a patient. Surrogate electrical activation information or data of one or more regions of a patient's heart may be monitored, or determined, using electrode apparatus 110 as shown in FIG. 1 and in FIG. 2-3. The exemplary electrode apparatus 110 may be configured to measure body-surface potentials of a patient 120 and, more particularly, torso-surface potentials of a patient 120. As shown in FIG. 2, the exemplary electrode apparatus 110 may include a set, or array, of electrodes 112, a strap 113, and interface/amplifier circuitry 116. In at least one embodiment, a portion of the set of electrodes may be used wherein the portion corresponds to a particular location on the patient's heart. The electrodes 112 may be attached, or coupled, to the strap 113 and the strap 113 may be configured to be wrapped around the torso of a patient 120 such that the electrodes 112 surround the patient's heart. As further illustrated, the electrodes 112 may be positioned around the circumference of a patient 120, including the posterior, lateral, posterolateral, anterolateral, and anterior locations of the torso of a patient 120.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 120. Further, in other examples, electrodes 112 (e.g., arranged in an array) may be part of, or located within, patches, vests, and/or other manners of securing the electrodes 112 to the torso of the patient 120.

The electrodes 112 may be configured to surround the heart of the patient 120 and record, or monitor, the electrical signals associated with the depolarization and repolarization of the heart after the signals have propagated through the torso of a patient 120. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. The computing apparatus 140 may be configured to analyze the signals from the electrodes 112 to provide as anterior-septal electrode signals and surrogate cardiac electrical activation times, e.g., representative of actual, or local, electrical activation times of one or more anterior-septal regions of the patient's heart, as will be further described herein, e.g., for use in evaluation of VfA pacing therapy. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a patient's cardiac condition and/or ventricle from atrium pacing therapy being delivered to the patient.

Figure 3:
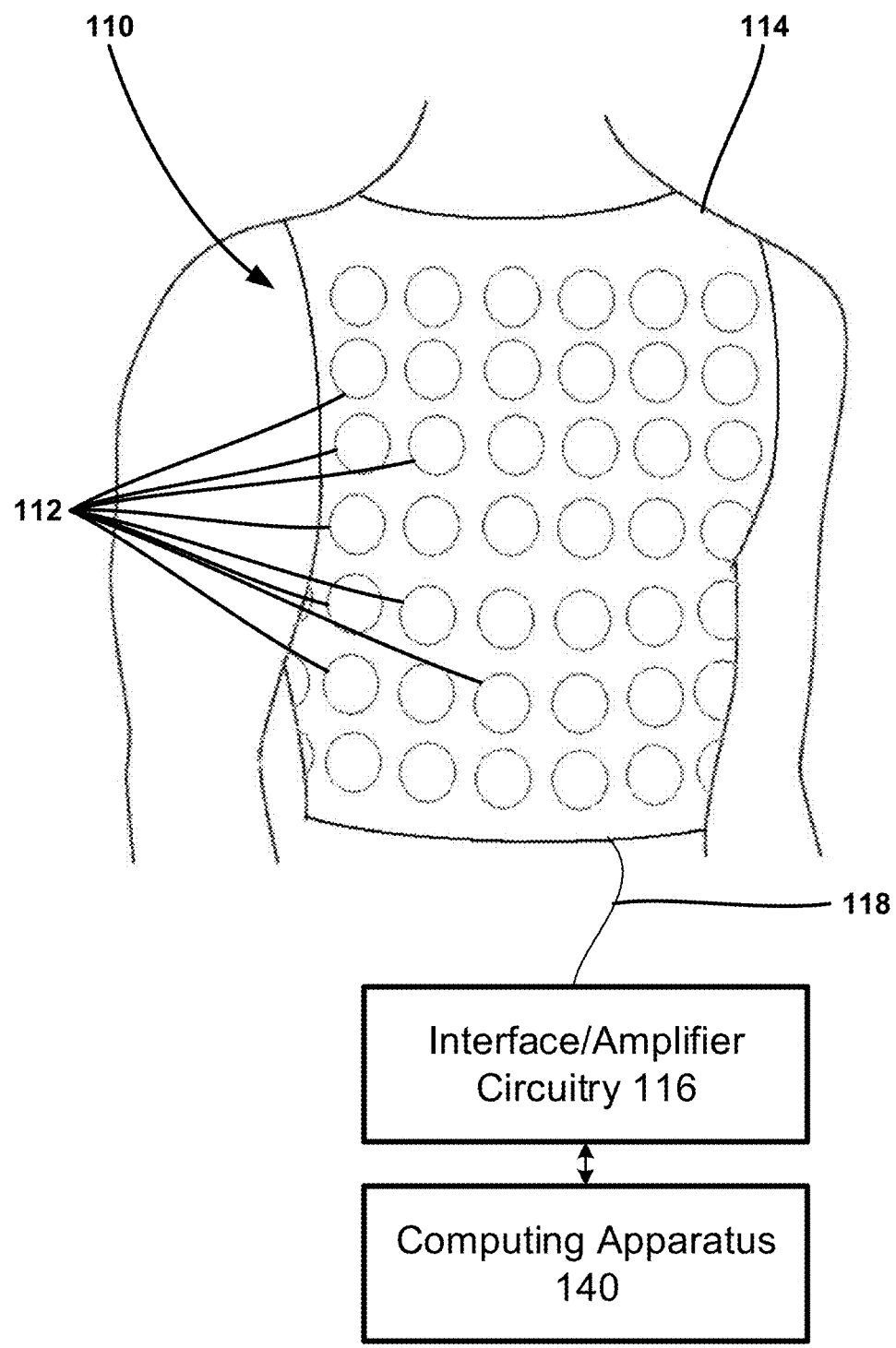

FIG. 3 illustrates another exemplary electrode apparatus 110 that includes a plurality of electrodes 112 configured to surround the heart of the patient 120 and record, or monitor, the electrical signals associated with the depolarization and repolarization of the heart after the signals have propagated through the torso of the patient 120. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 120, including, for example, the anterior, lateral, posterolateral, anterolateral, and posterior surfaces of the torso of the patient 120.

The vest 114 may be formed of fabric with the electrodes 112 attached to the fabric. The vest 114 may be configured to maintain the position and spacing of electrodes 112 on the torso of the patient 120. Further, the vest 114 may be marked to assist in determining the location of the electrodes 112 on the surface of the torso of the patient 120. In one or more embodiments, the vest 114 may include 17 or more anterior electrodes positionable proximate the anterior torso of the patient, and 39 or more posterior electrodes positionable proximate the anterior torso of the patient. In some examples, there may be about 25 electrodes 112 to about 256 electrodes 112 distributed around the torso of the patient 120, though other configurations may have more or less electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart. In at least one example, activation times of the anterior-septal region of a patient's heart can be approximated from surface ECG activation times measured using surface electrodes in proximity to surface areas corresponding to the anterior-septal region of the patient's heart. That is, a portion of the set of electrodes 112, and not the entire set, can be used to generate activation times corresponding to a particular location of the patient's heart that the portion of the set of electrodes corresponds to.

The exemplary systems, methods, and interfaces may be used to provide noninvasive assistance to a user in the evaluation of a patient's cardiac health or status, and/or the evaluation of cardiac therapy such as ventricle from atrium (VfA) pacing therapy by use of the electrode apparatus 110 (e.g., cardiac therapy being presently-delivered to a patient during implantation or after implantation). Further, the exemplary systems, methods, and interfaces may be used to assist a user in the configuration of the cardiac therapy, such as VfA pacing therapy, being delivered to a patient.

VfA pacing can be described as providing a synchronized homogeneous activation of ventricles of the heart. As an example, patients with atrial-ventricular (AV) block or prolonged AV timings that can lead to heart failure who have otherwise intact (e.g., normal) QRS can benefit from VfA pacing therapy. In addition, as an example, VfA pacing may provide beneficial activation for heart failure patients with intrinsic ventricular conduction disorders. Further, proper placement of VfA pacing can provide optimal activation of the ventricles for such patients. Further, left ventricular (LV) resynchronization for heart failure patients with left bundle branch block (LBBB) may find that VfA pacing enables easier access to left ventricular endocardium without exposing the leadless device or lead to endocardial blood pool. At the same time, in that example, this can help engage part of the conduction system to potentially correct LBBB and effectively resynchronize the patient.

Figure 4:
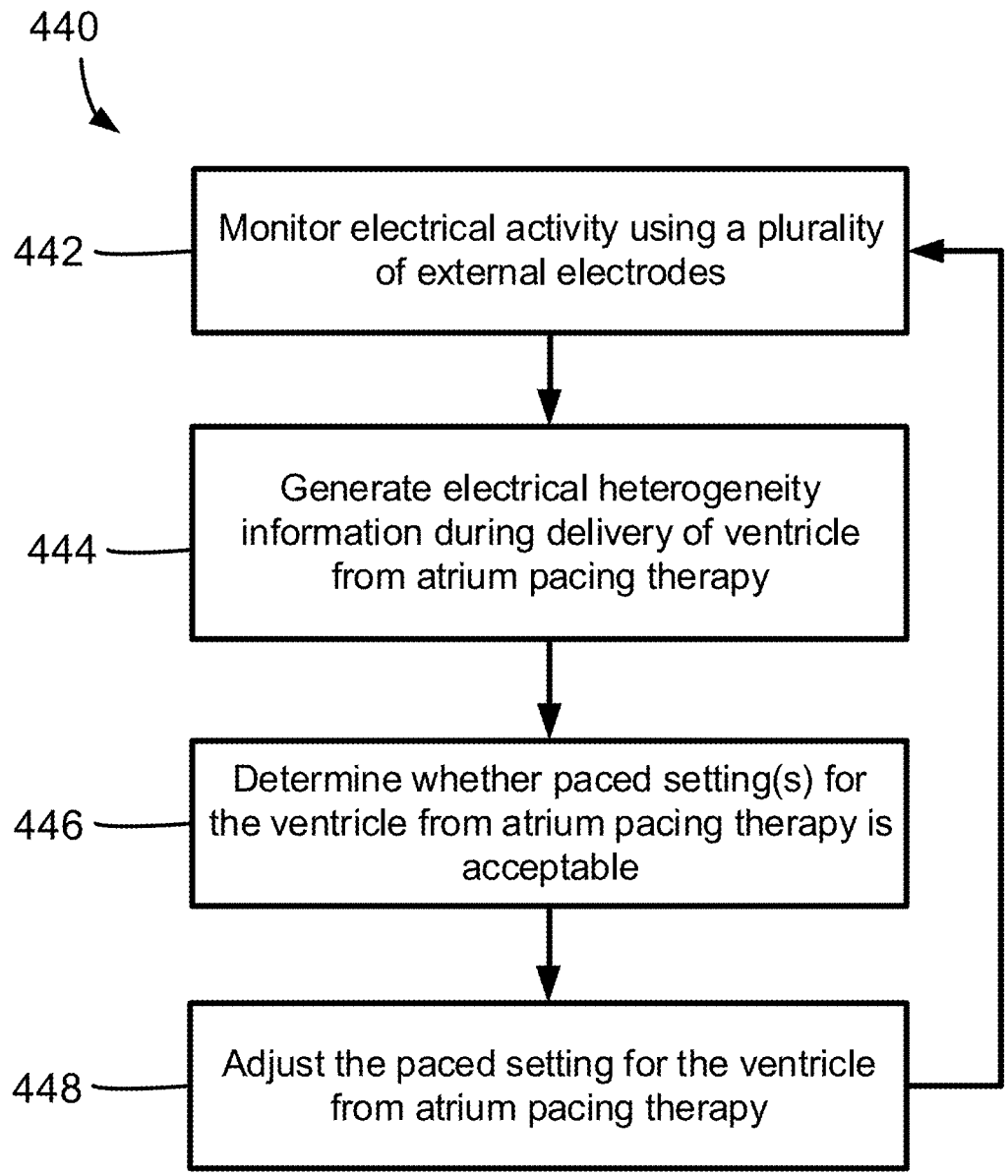
FIG. 4 is a block diagram of an exemplary method of evaluation of ventricle from atrium pacing therapy.

An exemplary method 440 of evaluation of VfA pacing is illustrated in FIG. 4. The method 440 can include monitoring electrical activity using a plurality of external electrodes 442, such as electrodes 112 described herein with reference to FIGS. 1-3. The electrical activity can be monitored by a plurality of electrodes during VfA pacing therapy or in the absence of VfA pacing therapy. The monitored electrical activity can be used to evaluate VfA pacing therapy to a patient using, e.g., the exemplary system described herein with respect to FIGS. 1-3. The electrical activity monitored using the ECG belt described above can be used to evaluate at least one paced setting of the VfA pacing therapy on the heart. As an example, a paced setting can be any one parameter or a combination of parameters including, but not limited to, electrode position, pacing polarity, pacing output, pacing pulsewidth, timing at which VfA pacing is delivered relative to atrial (A) timing, pacing rate, etc. Further, as an example, the location of the leadless device or a pacing lead can include a location in the left ventricle, accessed through the right atrium within, or in close proximity to, the high posterior basal and/or septal (HPBS) area of the left ventricular cavity. Moreover, pacing of, or in close proximity to, the HPBS area can be selective (e.g., involving stimulation of a particular area of the HPBS alone) or non-selective (e.g., combined pacing at the location of the HPBS and other atrial and/or ventricular septum areas).

Further, body-surface isochronal maps of ventricular activation can be constructed using the monitored electrical activity during VfA pacing therapy or in the absence of VfA pacing therapy. The monitored electrical activity and/or the map of ventricular activation can be used to generate electrical heterogeneity information. The electrical heterogeneity information can include determining metrics of electrical heterogeneity. The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces, which are more proximal to the left ventricle. The metrics of electrical heterogeneity information can include a metric of mean right ventricular activation time (RVAT) of electrodes on the right side of the torso of the patient. A metric of RVAT may be determined from electrodes on both the anterior and posterior surfaces which are more proximal to the right ventricle. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso. The metrics of electrical heterogeneity information can include a metric of anterior-septal activation times (ASAT) of electrodes on the torso in close proximity to the anterior-septal portion of the heart.

Thus, the method 440 can include generating electrical heterogeneity information during delivery of VfA pacing therapy at one or more VfA paced settings 444. The electrical heterogeneity information can be generated using metrics of electrical heterogeneity. As an example, the metrics of electrical heterogeneity can include at least one of an SDAT, an LVAT, an RVAT, an mTAT, and an ASAT. In at least one embodiment, only ASAT may be determined and further used by method 440, and/or ASAT may be more heavily weighted than other values.

The method 440 can include determining whether one or more paced settings associated with the VfA pacing therapy are acceptable 446. A paced setting can include a plurality of pacing parameters. The plurality of pacing parameters can be acceptable if the patient's cardiac condition improves, if the VfA pacing therapy is effectively capturing a desired portion of the left ventricle (e.g., the high posterior basal and/or septal area), and/or if a metric of electrical heterogeneity improves by a certain threshold compared to a baseline rhythm or therapy. In at least one embodiment, the determination of whether the paced setting is acceptable can be based on at least one metric of electrical heterogeneity generated from electrical activity during VfA pacing (and also, in some embodiments, during native conduction, or in the absence of VfA pacing). The at least one metric can include at least one of an SDAT, an LVAT, an RVAT, an mTAT, an ASAT.

Further, the plurality of pacing parameters can be acceptable if a metric of electrical heterogeneity is greater than or less than a particular threshold, and/or if the location of the pacing therapy to excite the left ventricle causes a particular pattern of excitation of the muscle fibers in the heart. In addition, the plurality of pacing parameters can be acceptable if a metric of electrical heterogeneity indicates a correction of a left bundle branch block (LBBB), and/or if a metric of electrical heterogeneity indicates a complete engagement of a Purkinje system, etc. As an example, a metric of electrical heterogeneity of an ASAT less than or equal to a threshold (e.g., a threshold of 30 ms) and an LVAT less than or equal to a threshold (e.g., a threshold of 30 ms) can indicate a correction of an LBBB, and thus, the paced setting is acceptable. As an example, a metric of electrical heterogeneity of an RVAT less than or equal to a threshold (e.g., a threshold of 30 ms), an ASAT less than or equal to a threshold (e.g., a threshold of 30 ms), and an LVAT less than or equal to a threshold (e.g., a threshold of 30 ms) can indicate a complete engagement of the Purkinje system, and thus the paced setting is acceptable.

The paced setting can be determined to be acceptable in response to the VfA pacing therapy using the paced setting being optimal, being beneficial, being indicative of complete engagement of patient's native cardiac conduction system, being indicative of correction of a ventricular conduction disorder (e.g., left bundle branch block), etc. A paced setting can include at least one of a pacing electrode position (including at least one of a depth, an angle, an amount of turn for a screw-based fixation mechanism, etc.), a voltage, a pulse width, an intensity, a pacing polarity, a pacing vector, a pacing waveform, a timing of the pacing delivered relative to an intrinsic or paced atrial event or relative to the intrinsic His bundle potential, and/or a pacing location, etc. A pacing vector can include any two or more pacing electrodes such as, e.g., a tip electrode to a can electrode, a tip electrode to a ring electrode etc., that are used to deliver the VfA pacing therapy, etc. The pacing location can refer to the location of any of the one or more pacing electrodes that are positioned using a lead, a leadless device, and/or any device or apparatus configured to deliver VfA, as will be further described in association with FIGS. 8-12.

The method 440 can include adjusting a paced setting for VfA pacing therapy 448. In at least one embodiment, the paced setting can be adjusted in response to the paced setting being unacceptable. In at least one embodiment, the paced setting can be adjusted in response to the paced setting being within an acceptable range but in order to determine whether the paced setting can be at a position within the acceptable range that is more beneficial, more useful, more functional, etc. for the VfA pacing therapy. As an example, when the paced setting is a location that the VfA pacing therapy is administered within a patient, the paced setting (e.g., location, depth of penetration of helical electrode, angle of helical electrode, etc.) can be adjusted until the VfA pacing therapy results in a metric of electrical heterogeneity that is above or below a threshold metric of electrical heterogeneity. That is, the paced setting can be adjusted to assist in placement of a lead, leadless device, and/or other electrical device to administer the VfA pacing therapy. In another embodiment, the paced setting could be adjusted to find the most optimal metric of electrical heterogeneity.

For example, pacing of the left ventricle can utilize a pacing electrode that includes anywhere from an approximately 4 millimeter (mm) long helix to an approximately 12 mm long helix, and the exemplary method 440 may be used to gradually titrate navigating the electrode up to a 4 mm depth, or some other particular depth. In at least one example, the pacing electrode includes an 8 mm long helix. More specifically, the pacing electrode may be partially screwed into or through a posterior basal area of the right atrium. Further, the pacing electrode may pass through the right atrium and be screwed into, attached to, or brought into close proximity to a location in the left ventricle. This location of the left ventricle can include a high posterior basal and/or septal area of the left ventricle where the VfA pacing may be performed, electrical activity may be monitored 442 during such VfA pacing, electrical heterogeneity information may be generated 444, and it may be determined whether the pacing setting, which in this case, may be an electrode location including depth and/or angle, is acceptable 446. Next, the paced setting, which in this case may be a location including depth and/or angle, may be adjusted 448. Thus, the pacing electrode may be screwed in, or through, the right atrium to be positioned in close proximity to or deeper within tissue in order to gain access to the left ventricle, and the method 440 may reiterate or be repeated until such desired location is achieved. In other words, the exemplary method 440 may indicate to a doctor to gradually slow down turning of the helix electrode through the right atrium allowing it to gain access to the left ventricle and be in close proximity to a portion of the left ventricle (e.g., the high posterior basal and/or septal area).

Further, in one or more embodiments, a determination of whether the paced setting is acceptable can be based on a particular metric of electrical heterogeneity using an ECG belt. For example, when a paced setting is associated with a first metric value of electrical heterogeneity, an indication (e.g., a display, a prompt, etc.) to turn a pacing electrode helix a particular number of turns can be made (e.g., to adjust the depth and/or angle of implant of the pacing electrode helix). In response to the paced setting being associated with a second metric value of electrical heterogeneity, an indication to stop turning the pacing electrode helix can be made. Furthermore, based on a metric of electrical heterogeneity, an indication of how many more turns of the pacing electrode helix can be indicated to assist in determining how much further to go with the pacing electrode helix. These indications can be displayed on a GUI of a monitor to assist in adjusting the paced setting and/or be on any number of display and/or notification devices.

In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

In at least one example, the paced setting (e.g., location including depth and/or angle) can be adjusted until the VfA pacing therapy results in a correction of bundle branch block (BBB) (or, more specifically, left BBB (LBBB). BBB can refer to a condition in which a delay and/or obstruction along a pathway that the electrical activity of the heart of the patient travels in order for the heart to properly beat. The delay and/or blockage may occur on the pathway that sends electrical impulses to the left or right side of the ventricles of the heart. The paced setting can be adjusted until the delay and/or blockage along the pathway is remedied, which can be indicated by a change in the metric of electrical heterogeneity, the metric of electrical heterogeneity being above or below a particular threshold, and/or any number of electrical information that may indicate that the BBB has been corrected.

In at least one example, the paced setting can be adjusted until the metric of electrical heterogeneity indicating a delay and/or blockage of BBB reaches a particular threshold metric. The metric of electrical heterogeneity being at the particular threshold metric can indicate the BBB has been corrected. The paced setting can be adjusted at a greater rate while the metric of electrical heterogeneity is further from the particular threshold metric and adjusted at a slower rate as the metric of electrical heterogeneity gets closer to the particular threshold metric. More specifically in response to at least one metric of electrical heterogeneity such as ASAT and LVAT being below a threshold, such as below 30 milliseconds (ms) for each of ASAT and LVAT, an indication of a correction of LBBB can be determined.

In at least one embodiment, the electrical heterogeneity information can be generated while delivering VfA pacing cardiac therapy using a selected first paced setting. In response to the selected first paced setting being determined to be an unacceptable paced setting, a selected second paced setting can be used. As an example, the first paced setting can include a first location of an electrode in the left ventricle, by way of going through the right atrium a first distance. In response to the first location not being indicated as an acceptable location evaluated at one or more pacing voltages, polarities, or timings, a second location within the left ventricle, associated with a second distance through the right atrium, can be used for delivering the VfA pacing therapy.

Lead placement at a site at, or in close proximity to, a particular location in the left ventricle (e.g., basal and/or septal area of the left ventricular myocardium) can be determined using the method described above. In at least one example, the method can be performed during implant placement. A decision-making process to determine whether to use the tested location (e.g., a first location) or to try for an additional location (e.g., a second location) for better results could be based on an automated system. As an example, parameters can be set to indicate whether the location is acceptable and when those parameters are met, the system automatically accepts the paced settings (e.g., location for VfA pacing using a lead or leadless device). In response to a determination that the VfA pacing therapy is not acceptable (e.g., the VfA paced setting used to deliver the VfA pacing therapy), the VfA paced setting can be changed. In response to changing the paced setting, a determination of whether the changed VfA paced setting for the VfA pacing therapy is acceptable based on the electrical heterogeneity information generated from the electrical activity using the plurality of external electrodes during delivery of VfA pacing therapy using the changed VfA paced setting can be performed. In at least one example, the data from the metrics of electrical heterogeneity can be provided to a clinician and the clinician can make the decision whether to accept the paced setting (e.g., a location for VfA pacing using a lead or leadless device).

In at least one embodiment, a metric of electrical heterogeneity used to determine whether a paced setting is acceptable can be used to compare VfA pacing therapy to cardiac resynchronization therapy (CRT). A metric of electrical heterogeneity while performing CRT can be generated. Then, as an example, the metric of electrical heterogeneity for CRT can be compared to the metric of electrical heterogeneity for VfA pacing.

FIG. 5 is a detailed block diagram of another exemplary method 550 of evaluating VfA pacing therapy. The method 550 can include monitoring electrical activity using a plurality of external electrodes 552, such as electrodes 112 described herein with reference to FIGS. 1-3. The electrical activity can be monitored by a plurality of electrodes during VfA pacing therapy or in the absence of VfA pacing therapy. The monitored electrical activity can be used to evaluate VfA pacing therapy to a patient using, e.g., the exemplary system described herein with respect to FIGS. 1-3. The electrical activity monitored using the ECG belt described above can be used to evaluate at least one paced setting of the VfA pacing therapy on the heart.

The method 550 can include generating baseline electrical heterogeneity information (EHI) 554. The baseline EHI can be generated in the absence of VfA pacing therapy. That is, the baseline EHI can be generated from electrical activity that is monitored in the absence of the VfA pacing therapy. The baseline EHI can include a baseline metric of electrical heterogeneity. A baseline metric can refer to a metric generated during native AV conduction in the absence of VfA pacing therapy to a patient or a metric generated during previous VfA pacing therapy using different settings or parameters or a metric generated during other cardiac pacing (e.g., more conventional cardiac pacing such as right ventricular pacing). The baseline metric can include at least one of an SDAT, an LVAT, an RVAT, an mTAT, and an ASAT. In one embodiment, an ASAT only baseline metric can be used.

The method 550 can include generating paced electrical heterogeneity information (EHI) during delivery of VfA pacing therapy 556. The paced EHI can include a therapy metric of electrical heterogeneity. A therapy metric can refer to a metric generated while delivering VfA pacing therapy to a patient. The therapy metric can include at least one of an SDAT, an LVAT, an RVAT, an mTAT, and an ASAT.

The method 550 can include comparing the baseline EHI to the paced EHI 558. Comparing the baseline EHI to the paced EHI can include comparing a baseline metric of electrical heterogeneity of the baseline EHI to a therapy metric of electrical heterogeneity of the paced EHI. As an example, a baseline SDAT can be compared to a therapy SDAT, a baseline LVAT can be compared to a therapy LVAT, a baseline RVAT can be compared to a therapy RVAT, a baseline mTAT can be compared to a therapy mTAT, and a baseline ASAT can be compared to a therapy ASAT. Further, for example, in at least one embodiment, a relative percentage difference between one or more metrics of EH generated during delivery of VfA pacing therapy and one or more baseline metrics of EH (either in the absence of delivery of VfA pacing therapy or during previous settings of VfA pacing therapy) may be compared to a threshold percentage. In one embodiment, an baseline ASAT metric of EH can be compared to a paced ASAT metric of EH.

The method 550 can include determining whether a paced setting for the VfA pacing therapy is acceptable based on the comparison 560. A selected paced setting can be used to deliver the VfA pacing therapy and electrical heterogeneity information can be generated while using the paced setting. The determination of whether the paced setting is acceptable can be based on the comparison of the baseline EHI to a therapy EHI while using the paced setting. As an example, VfA pacing using the paced setting may be considered acceptable if the relative percentage difference (e.g., reduction) in EH with pacing compared to EH without pacing is less than or equal or greater than or equal to a percentage threshold. More specifically, in at least one embodiment, the one or more metrics of EH may be SDAT, LVAT, RVAT, mTAT, ASAT, or any combination thereof, and the selected percentage threshold may be between about 1% to about 15%. In at least one embodiment, the selected percentage threshold for the absolute relative difference (e.g., reduction) in EH with VfA pacing compared to without VfA pacing is 5%. In one or more other embodiments the selected percentage may be less than or equal to or greater than or equal to 2%, less than or equal to or greater than or equal to 3%, less than or equal to or greater than or equal to 6%, less than or equal to or greater than or equal to 9%, less than or equal to or greater than or equal to 10%, less than or equal to or greater than or equal to 15%, etc.

In at least one embodiment, as an example, the threshold percentage can be 5% for each of SDAT and LVAT. Thus, in this embodiment, if the change (e.g., reduction) in SDAT from baseline conduction to VfA pacing therapy is greater than or equal to 5% and the change (e.g., reduction) in LVAT from baseline conduction to VfA pacing therapy is greater than or equal to 5%, it may be determined that the VfA pacing therapy is acceptable. Conversely, if the change (e.g., relative reduction) in SDAT from baseline conduction to VfA pacing therapy is less than 5% and the change (e.g., relative reduction) in LVAT from baseline conduction to VfA pacing therapy is less than 5%, it may be determined that the VfA pacing therapy is unacceptable. The threshold reduction of metrics of electrical heterogeneity (e.g., reduction of electrical dyssynchrony) from baseline to pacing can indicate an improvement in resynchronization of the patient's heart.

Additionally, although the comparison of EH metrics to thresholds and the comparison of the percentage difference between EH metrics generated during delivery of VfA pacing therapy and EH baseline metrics are described separately, it is to be understood that each process may be used by itself or together to determine whether the Vfa pacing therapy is acceptable (or more specifically, whether one or more parameters of the VfA pacing therapy are acceptable).

The method 550 can further include adjusting the paced setting for the VfA pacing therapy 562. The adjustment of the paced setting can be performed in response to the determination 560 that the paced setting for the VfA pacing therapy is acceptable. In this example, the paced setting could be adjusted to find a paced setting that is more acceptable than the already accepted paced setting. That is, a paced setting may be acceptable due to corresponding therapy EHI being within an acceptable range but adjusting to another paced setting may result in therapy EHI that is closer to a particular portion of the range that is more acceptable. Further, in at least one embodiment, the adjustment of the paced setting can be performed in response to the determination 560 that the paced setting for the VfA pacing therapy is unacceptable.

In response to the paced setting being adjusted, the process can repeat, starting with monitoring electrical activity 552, generating baseline EHI 554, generating paced EHI 556, comparing baseline EHI to therapy EHI 558, and determining whether the paced setting is acceptable 560. This iterative process can repeat until either a paced setting is determined to be acceptable or the paced setting is within acceptable ranges, etc. As an example, where the paced setting is one of location, the location (including at least one of depth and angle) of an implantable electrode for delivering VfA pacing therapy can be adjusted, and this process repeated, until the therapy EHI associated with a particular location of the implantable electrode is acceptable.

Figure 6:
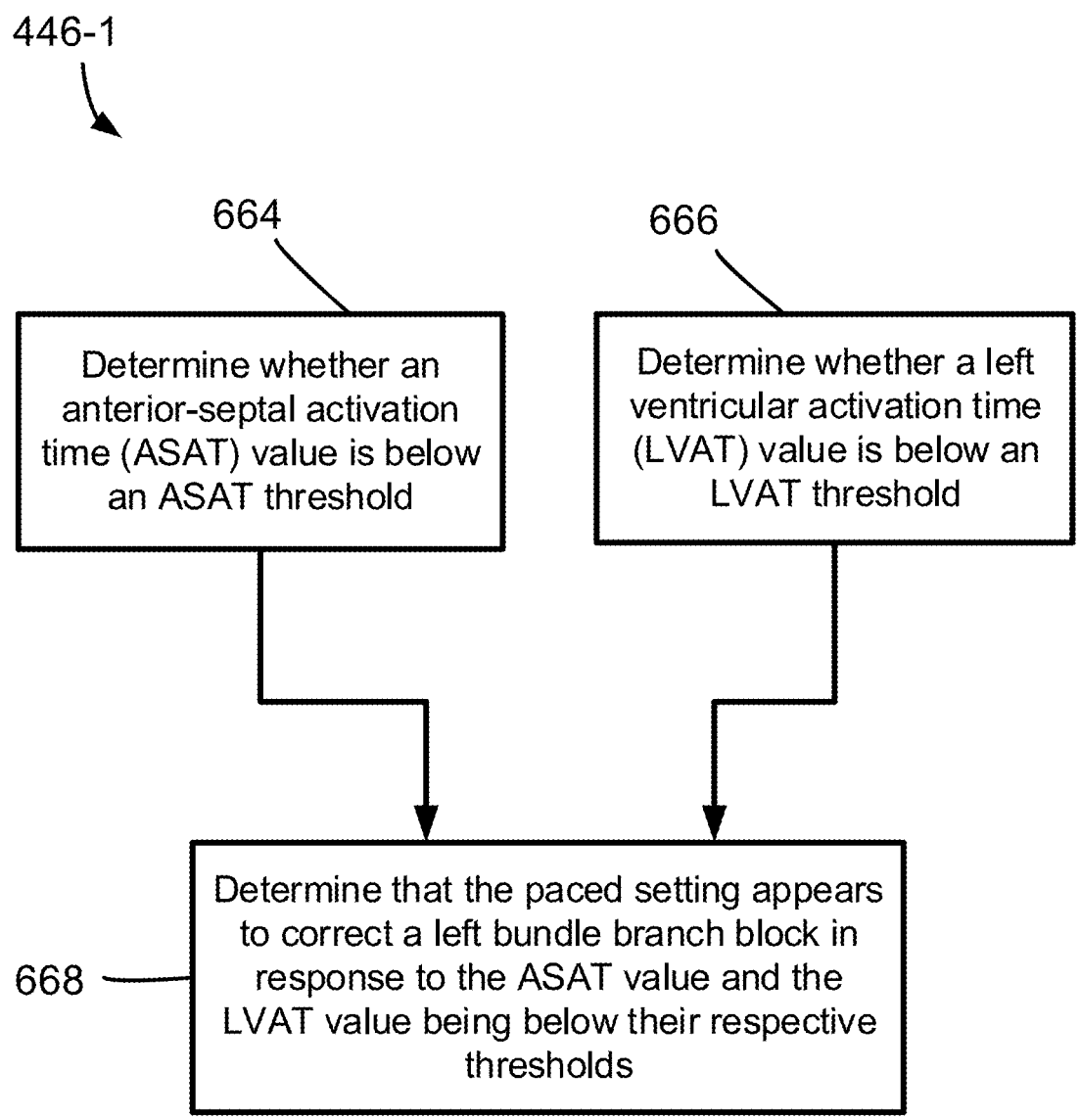
FIG. 6 is a block diagram of another exemplary method of evaluation of ventricle from atrium pacing therapy.

FIG. 6 is a block diagram of another exemplary method 446-1 of evaluation of ventricle from atrium pacing therapy. The method 446-1 can be described as one exemplary embodiment of method step 446 in method 440 described in association with FIG. 4. That is, determining whether paced setting(s) for the VfA pacing therapy is acceptable 446 of method 440 can include the steps of method 446-1 in FIG. 6. The method 446-1 can include determining whether an anterior-septal activation time (ASAT) value is equal to or less than an ASAT threshold 664. An anterior-septal region may be described as referring to a location in front of the interventricular septum, which refers to the curved slanting wall that separates the right and left ventricles of the heart and is composed of a muscular lower part and a thinner more membranous upper part. The ASAT value can be a value generated from electrical activity gathered by external electrodes in close proximity to the anterior-septal region or whose electrical activity corresponds to the anterior-septal region. In at least one example, the ASAT threshold can be 30 ms. The ASAT threshold can be greater than or equal to about 20 ms, greater than or equal to about 30 ms, greater than or equal to about 40 ms, greater than or equal to about 50 ms, greater than or equal to about 60 ms, etc. Also, the ASAT threshold can be less than or equal to about 25 ms, less than or equal to about 35 ms, less than or equal to about 45 ms, less than or equal to about 55 ms, etc.

The method 446-1 can include determining whether a left ventricular activation time (LVAT) value is below an LVAT threshold 666. The LVAT value can be a value generated from electrical activity gathered by external electrodes in close proximity to the left ventricular region or whose electrical activity corresponds to the left ventricular region. In at least one example, the LVAT threshold can be 30 ms. The LVAT threshold can be greater than or equal to about 20 ms, greater than or equal to about 30 ms, greater than or equal to about 40 ms, greater than or equal to about 50 ms, greater than or equal to about 60 ms, etc. Also, the LVAT threshold can be less than or equal to about 25 ms, less than or equal to about 35 ms, less than or equal to about 45 ms, less than or equal to about 55 ms, etc.

The method 446-1 can include determining that the paced setting appears to correct a left bundle branch block (LBBB) in response to the ASAT value and the LVAT value being below their respective thresholds 668. As an example, the ASAT value can be less than or equal to a threshold of 30 ms and the LVAT value can be less than or equal to a threshold of 30 ms in order to indicate that the LBBB has been corrected. In at least one example, the ASAT threshold can be greater than or equal to 20 ms and the LVAT threshold can be greater than or equal to 20 ms, the ASAT threshold can be greater than or equal to 25 ms and the LVAT threshold can be greater than or equal to 25 ms, the ASAT threshold can be greater than or equal to 20 ms and the LVAT threshold can be greater than or equal to 30 ms, the ASAT threshold can be greater than or equal to 30 ms and the LVAT threshold can be greater than or equal to 20 ms, and so forth for any combination of ASAT and LVAT thresholds. Also, the ASAT threshold can be less than or equal to 20 ms and the LVAT threshold can be less than or equal to 20 ms, the ASAT threshold can be less than or equal to 25 ms and the LVAT threshold can be less than or equal to 25 ms, the ASAT threshold can be less than or equal to 20 ms and the LVAT threshold can be less than or equal to 30 ms, the ASAT threshold can be less than or equal to 30 ms and the LVAT threshold can be less than or equal to 20 ms, and so forth for any combination of ASAT and LVAT thresholds. Thus, if during VfA pacing, the ASAT is less than or equal to a ASAT threshold and the LVAT is less than equal to an LVAT threshold, it may be determined that the VfA pacing therapy is correcting the LBBB.

Figure 7:
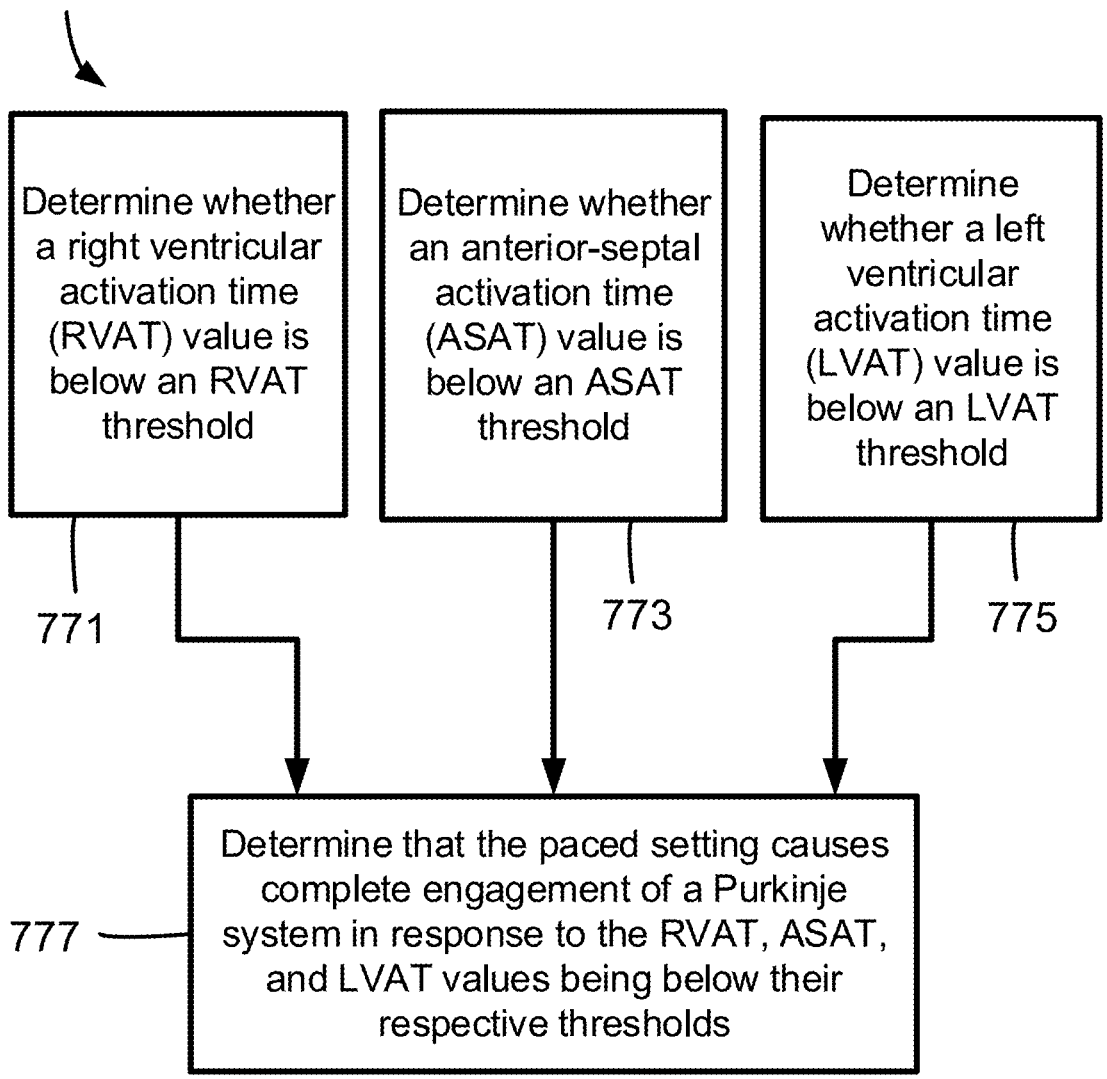
FIG. 7 is a block diagram of another exemplary method of evaluation of ventricle from atrium pacing therapy.

FIG. 7 is a block diagram of another exemplary method 446-2 of evaluation of ventricle from atrium pacing therapy. The method 446-2 can be described as one exemplary embodiment of method step 446 in method 440 described in association with FIG. 4. That is, determining whether paced setting(s) for the VfA pacing therapy is acceptable 446 of method 440 can include the steps of method 446-2 in FIG. 6. The method 446-2 can include determining whether a right ventricular activation time (RVAT) value is equal to or less than an RVAT threshold 771. The RVAT value can be a value generated from electrical activity gathered by external electrodes in close proximity to the right ventricular region or whose electrical activity corresponds to the right ventricular region. In at least one example, the RVAT threshold can be 30 ms. In at least one example, the RVAT threshold can be 30 ms. The RVAT threshold can be greater than or equal to about 20 ms, greater than or equal to about 30 ms, greater than or equal to about 40 ms, greater than or equal to about 50 ms, greater than or equal to about 60 ms, etc. Also, the RVAT threshold can be less than or equal to about 25 ms, less than or equal to about 35 ms, less than or equal to about 45 ms, less than or equal to about 55 ms, etc.

The method 446-2 can include determining whether an anterior-septal activation time (ASAT) value is equal to or less than an ASAT threshold 773. An anterior-septal region can refer to a location in front of the interventricular septum, which refers to the curved slanting wall that separates the right and left ventricles of the heart and is composed of a muscular lower part and a thinner more membranous upper part. The ASAT value can be a value generated from electrical activity gathered by external electrodes in close proximity to the anterior-septal region or whose electrical activity corresponds to the anterior-septal region. In at least one example, the ASAT threshold can be 30 ms. The ASAT threshold can be greater than or equal to about 20 ms, greater than or equal to about 30 ms, greater than or equal to about 40 ms, greater than or equal to about 50 ms, greater than or equal to about 60 ms, etc. Also, the ASAT threshold can be less than or equal to about 25 ms, less than or equal to about 35 ms, less than or equal to about 45 ms, less than or equal to about 55 ms, etc.

The method 446-2 can include determining whether a left ventricular activation time (LVAT) value is equal to or less than an LVAT threshold 775. The LVAT value can be a value generated from electrical activity gathered by external electrodes in close proximity to the right ventricular region or whose electrical activity corresponds to the right ventricular region. In at least one example, the LVAT threshold can be 30 ms. The LVAT threshold can be greater than or equal to about 20 ms, greater than or equal to about 30 ms, greater than or equal to about 40 ms, greater than or equal to about 50 ms, greater than or equal to about 60 ms, etc. Also, the LVAT threshold can be less than or equal to about 25 ms, less than or equal to about 35 ms, less than or equal to about 45 ms, less than or equal to about 55 ms, etc.

The method 446-2 can include determining that the paced setting causes complete engagement of a Purkinje system in response to the RVAT, ASAT, and LVAT values being below their respective thresholds 777. As an example, the RVAT value can be less than or equal to a threshold of 30 ms, an ASAT value can be less than or equal to a threshold of 30 ms, and an LVAT value can be less than or equal to a threshold of 30 ms in order to indicate that there is complete engagement of the Purkinje system. The Purkinje system can be partially and/or completely engaged through the His bundle, or bundle of His, which refers to a collection of heart muscle cells specialized for electrical conduction. The His bundle can transmit electrical impulses from the atrial-ventricular (AV) node (located between the atria and ventricles) to a point of the apex of the fascicular branches via the bundle branches. The fascicular branches then lead to the Purkinje fibers, which can provide fast electrical conduction to the ventricles, thereby causing the cardiac muscle of the ventricles to contract more efficiently at a paced interval. Traditional cardiac pacing therapies have included electrical stimulation of ventricular muscle which provides an alternative pathway of electrical activation usually bypassing the fast conduction path provided by His bundle and Purkinje fibers, often resulting in slower cell to cell conduction and lower efficiency in cardiac contraction than that potentially achievable through successful stimulation of the His bundle.

In at least one example, the RVAT threshold can be less than, equal to, or greater than 20 ms, the ASAT threshold can be less than, equal to, or greater than 20 ms, and the LVAT threshold can be less than, equal to, or greater than 20 ms. In other example, the RVAT threshold can be less than, equal to, or greater than 25 ms, the ASAT threshold can be less than, equal to, or greater than 25 ms, and the LVAT threshold can be less than, equal to, or greater than 25 ms. In other example, the RVAT threshold can be less than, equal to, or greater than 20 ms, the ASAT threshold can be less than, equal to, or greater than 20 ms, and the LVAT threshold can be less than, equal to, or greater than 30 ms. In other example, the RVAT value can be less than, equal to, or greater than 30 ms, the ASAT threshold can be less than, equal to, or greater than 30 ms, and the LVAT threshold can be less than, equal to, or greater than 20 ms. In another example, the RVAT threshold can be 30 ms, the ASAT threshold can be 20 ms, and the LVAT threshold can be 30 ms, and so forth for any combination of RVAT, ASAT, and LVAT thresholds. Thus, if during VfA pacing, the RVAT is less than or equal to an RVAT threshold, the ASAT is less than or equal to an ASAT threshold, and the LVAT is less than equal to an LVAT threshold, it may be determined that there is complete and/or substantially complete engagement of the Purkinje system.

The exemplary systems, methods, and graphical user interfaces described herein may be used with respect to the implantation and configuration of an implantable medical device (IMD) and/or one or more leads configured to be located proximate one or more portions of a patient's heart, e.g., proximate a location in the left ventricle). For example, the exemplary systems, methods, and interfaces may be used in conjunction with an exemplary therapy system 10 described herein with reference to FIGS. 8-12.

Figure 8:
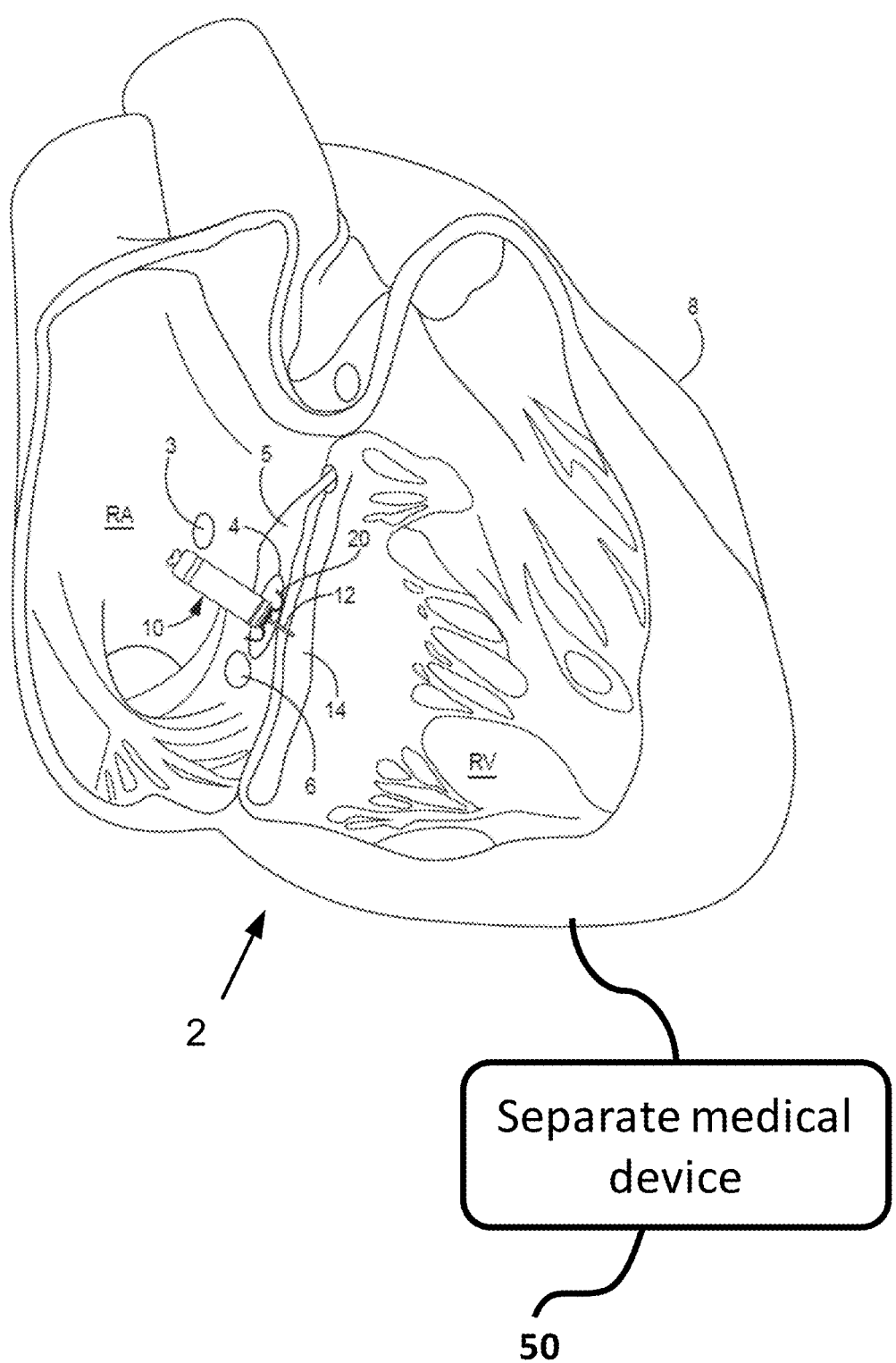
FIG. 8 is a conceptual diagram of an illustrative cardiac therapy system including an intracardiac medical device implanted in a patient's heart and a separate medical device positioned outside of the patient's heart.

Although the present disclosure describes leadless and leaded implantable medical devices, reference is first made to FIG. 8 showing a conceptual diagram of a cardiac therapy system 2 including an intracardiac medical device 10 that may be configured for single or dual chamber therapy and implanted in a patient's heart 8. In some embodiments, the device 10 may be configured for single chamber pacing and may, for example, switch between single chamber and multiple chamber pacing (e.g., dual or triple chamber pacing). As used herein, "intracardiac" refers to a device configured to be implanted entirely within a patient's heart, for example, to provide cardiac therapy. The device 10 is shown implanted in the right atrium (RA) of the patient's heart 8 in a target implant region 4. The device 10 may include one or more fixation members 20 that anchor a distal end of the device against the atrial endocardium in a target implant region 4. The target implant region 4 may lie between the Bundle of His 5 and the coronary sinus 3 and may be adjacent the tricuspid valve 6. The device 10 may be described as a ventricle-from-atrium (VfA) device, which may sense or provide therapy to one or both ventricles (e.g., right ventricle, left ventricle, or both ventricles, depending on the circumstances) while being generally disposed in the right atrium. In particular, the device 10 may include a tissue-piercing electrode that may be implanted in the basal and/or septal region of the left ventricular myocardium of the patient's heart from the triangle of Koch region of the right atrium through the right atrial endocardium and central fibrous body.

The device 10 may be described as a leadless implantable medical device. As used herein, "leadless" refers to a device being free of a lead extending out of the patient's heart 8. In other words, a leadless device may have a lead that does not extend from outside of the patient's heart to inside of the patient's heart. Some leadless devices may be introduced through a vein, but once implanted, the device is free of, or may not include, any transvenous lead and may be configured to provide cardiac therapy without using any transvenous lead. A leadless VfA device, in particular, does not use a lead to operably connect to an electrode in the ventricle when a housing of the device is positioned in the atrium. A leadless electrode may be coupled to the housing of the medical device without using a lead between the electrode and the housing.

The device 10 may include one or more dart electrode 12 having a straight shaft extending from the distal end region of device 10, through the atrial myocardium and the central fibrous body, and into the ventricular myocardium 14 or along the ventricular septum, without perforating entirely through the ventricular endocardial or epicardial surfaces. The dart electrode 12 may carry an electrode at the distal end region of the shaft for positioning the electrode within the ventricular myocardium for sensing ventricular signals and delivering ventricular pulses (e.g., to depolarize the left ventricle to initiate a contraction of the left ventricle). In some examples, the electrode at the distal end region of the shaft is a cathode electrode provided for use in a bipolar electrode pair for pacing and sensing. While the implant region 4 is shown in FIG. 8 to enable one or more electrodes of the one or more dart electrodes 12 to be positioned in the ventricular myocardium, it is recognized that a device having the aspects disclosed herein may be implanted at other locations for multiple chamber pacing (e.g., dual or triple chamber pacing), single chamber pacing with multiple chamber sensing, single chamber pacing and/or sensing, or other clinical therapy and applications as appropriate.

The cardiac therapy system 2 may also include a separate medical device 50 (depicted diagrammatically in FIG. 8), which may be positioned outside the patient's heart 8 (e.g., subcutaneously) and may be operably coupled to the patient's heart 8 to deliver cardiac therapy thereto. In one example, separate medical device 50 may be an extravascular ICD. In some embodiments, an extravascular ICD may include a defibrillation lead with a defibrillation electrode. A therapy vector may exist between the defibrillation electrode on the defibrillation lead and a housing electrode of the ICD. Further, one or more electrodes of the ICD may also be used for sensing electrical signals related to the patient's heart 8. The ICD may be configured to deliver shock therapy including one or more defibrillation or cardioversion shocks. For example, if an arrhythmia is sensed, the ICD may send a pulse via the electrical lead wires to shock the heart and restore its normal rhythm. In some examples, the ICD may deliver shock therapy without placing electrical lead wires within the heart or attaching electrical wires directly to the heart (subcutaneous ICDs). Examples of extravascular, subcutaneous ICDs that may be used with the system 2 described herein may be described in U.S. Pat. No. 9,278,229 (Reinke et al.), issued 8 Mar. 2016, which is incorporated herein by reference in its entirety.

In the case of shock therapy, e.g., the defibrillation shocks provided by the defibrillation electrode of the defibrillation lead, separate medical device 50 (e.g., extravascular ICD) may include a control circuit that uses a therapy delivery circuit to generate defibrillation shocks having any of a number of waveform properties, including leading-edge voltage, tilt, delivered energy, pulse phases, and the like. The therapy delivery circuit may, for instance, generate monophasic, biphasic, or multiphasic waveforms. Additionally, the therapy delivery circuit may generate defibrillation waveforms having different amounts of energy. For example, the therapy delivery circuit may generate defibrillation waveforms that deliver a total of between approximately 60-80 Joules (J) of energy for subcutaneous defibrillation.

The separate medical device 50 may include a sensing circuit. The sensing circuit may be configured to obtain electrical signals sensed via one or more combinations of electrodes and process the obtained signals. The components of the sensing circuit may be analog components, digital components, or a combination thereof. The sensing circuit may, for example, include one or more sense amplifiers, filters, rectifiers, threshold detectors, analog-to-digital converters (ADCs) or the like. The sensing circuit may convert the sensed signals to digital form and provide the digital signals to the control circuit for processing or analysis. For example, the sensing circuit may amplify signals from sensing electrodes and convert the amplified signals to multi-bit digital signals by an ADC. The sensing circuit may also compare processed signals to a threshold to detect the existence of atrial or ventricular depolarizations (e.g., P- or R-waves) and indicate the existence of the atrial depolarization (e.g., P-waves) or ventricular depolarizations (e.g., R-waves) to the control circuit.

The device 10 and the separate medical device 50 may cooperate to provide cardiac therapy to the patient's heart 8. For example, the device 10 and the separate medical device 50 may be used to detect tachycardia, monitor tachycardia, and/or provide tachycardia-related therapy. For example, the device 10 may communicate with the separate medical device 50 wirelessly to trigger shock therapy using the separate medical device 50. As used herein, "wirelessly" refers to an operative coupling or connection without using a metal conductor between the device 10 and the separate medical device 50. In one example, wireless communication may use a distinctive, signaling, or triggering electrical pulse provided by the device 10 that conducts through the patient's tissue and is detectable by the separate medical device 50. In another example, wireless communication may use a communication interface (e.g., an antenna) of the device 10 to provide electromagnetic radiation that propagates through patient's tissue and is detectable, for example, using a communication interface (e.g., an antenna) of the separate medical device 50.

Figure 9:
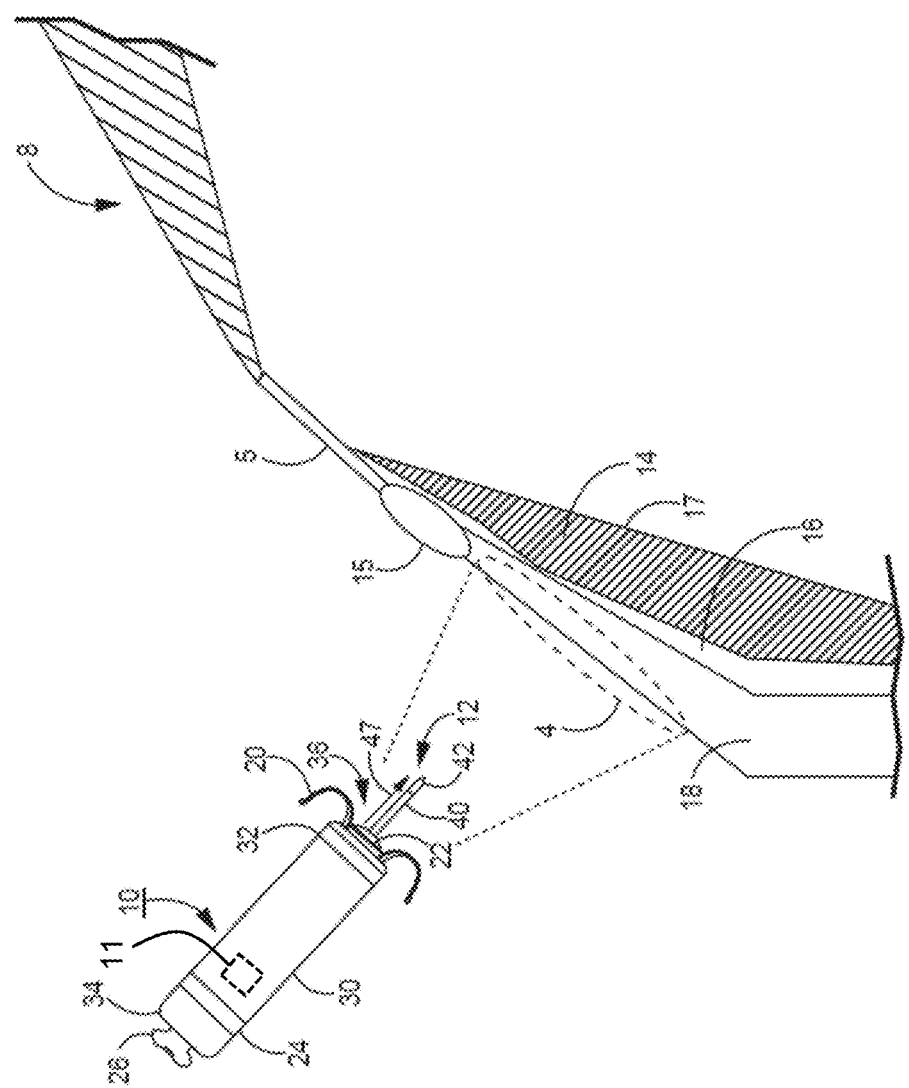
FIG. 9 is an enlarged conceptual diagram of the intracardiac medical device of FIG. 8 and anatomical structures of the patient's heart according to one example.

FIG. 9 is an enlarged conceptual diagram of the intracardiac medical device 10 and anatomical structures of the patient's heart 8. The intracardiac device 10 may include a housing 30. The housing 30 may define a hermetically sealed internal cavity in which internal components of the device 10 reside, such as a sensing circuit, therapy delivery circuit, control circuit, memory, telemetry circuit, other optional sensors, and a power source as generally described in conjunction with FIG. 11 below. The housing 30 may be formed from an electrically conductive material including titanium or titanium alloy, stainless steel, MP35N (a non-magnetic nickel-cobalt-chromium-molybdenum alloy), platinum alloy or other bio-compatible metal or metal alloy. In other examples, the housing 30 may be formed from a non-conductive material including ceramic, glass, sapphire, silicone, polyurethane, epoxy, acetyl co-polymer plastics, polyether ether ketone (PEEK), a liquid crystal polymer, or other biocompatible polymer.

The housing 30 may be described as extending between a distal end region 32 and a proximal end region 34 in a generally cylindrical shape to facilitate catheter delivery. In other embodiments, the housing 30 may be prismatic or any other shape so as to perform the functionality and utility described herein. The housing 30 may include a delivery tool interface member 26, e.g., at the proximal end 34, for engaging with a delivery tool during implantation of the device 10.

All or a portion of the housing 30 may function as an electrode during cardiac therapy, for example, in sensing and/or pacing. In the example shown, the housing-based electrode 24 is shown to circumscribe a proximal portion of the housing 30. When the housing 30 is formed from an electrically conductive material, such as a titanium alloy or other examples listed above, portions of the housing 30 may be electrically insulated by a non-conductive material, such as a coating of parylene, polyurethane, silicone, epoxy, or other biocompatible polymer, leaving one or more discrete areas of conductive material exposed to define the proximal housing-based electrode 24. When the housing 30 is formed from a non-conductive material, such as a ceramic, glass or polymer material, an electrically-conductive coating or layer, such as a titanium, platinum, stainless steel, or alloys thereof, may be applied to one or more discrete areas of the housing 30 to form the proximal housing-based electrode 24. In other examples, the proximal housing-based electrode 24 may be a component, such as a ring electrode, that is mounted or assembled onto the housing 30. The proximal housing-based electrode 24 may be electrically coupled to internal circuitry of the device 10, e.g., via the electrically-conductive housing 30 or an electrical conductor when the housing 30 is a non-conductive material.

In the example shown, the proximal housing-based electrode 24 is located nearer to the housing proximal end region 34 than the housing distal end region 32 and is therefore referred to as a "proximal housing-based electrode" 24. In other examples, however, the housing-based electrode 24 may be located at other positions along the housing 30, e.g., relatively more distally than the position shown.

At the distal end region 32, the device 10 may include a distal fixation and electrode assembly 36, which may include one or more fixation members 20, in addition to one or more dart electrodes 12 of equal or unequal length. The dart electrode 12 may include a shaft 40 extending distally away from the housing distal end region 32 and may include one or more electrode elements, such as a tip electrode 42 at or near the free, distal end region of the shaft 40. The tip electrode 42 may have a conical or hemi-spherical distal tip with a relatively narrow tip diameter (e.g., less than about 1 mm) for penetrating into and through tissue layers without using a sharpened tip or needle-like tip having sharpened or beveled edges.

The shaft 40 of the dart electrode 12 may be a normally straight member and may be rigid. In other embodiments, the shaft 40 may be described as being relatively stiff but still possessing limited flexibility in lateral directions. Further, the shaft 40 may be non-rigid to allow some lateral flexing with heart motion. However, in a relaxed state, when not subjected to any external forces, the shaft 40 may maintain a straight position as shown to hold the tip electrode 42 spaced apart from the housing distal end region 32 at least by the height 47 of the shaft 40. The dart electrode 12 may be configured to pierce through one or more tissue layers to position the tip electrode 42 within a desired tissue layer, e.g., the ventricular myocardium. As such, the height 47 of the shaft 40 may correspond to the expected pacing site depth, and the shaft may have a relatively high compressive strength along its longitudinal axis to resist bending in a lateral or radial direction when pressed against the implant region 4. If a second dart electrode 12 is employed, its length may be unequal to the expected pacing site depth and may be configured to act as an indifferent electrode for delivering of pacing energy to the tissue. A longitudinal axial force may be applied against the tip electrode 42, e.g., by applying longitudinal pushing force to the proximal end 34 of the housing 30, to advance the dart electrode 12 into the tissue within target implant region. The shaft 40 may be longitudinally non-compressive. The shaft 40 may be elastically deformable in lateral or radial directions when subjected to lateral or radial forces to allow temporary flexing, e.g., with tissue motion, but may return to its normally straight position when lateral forces diminish. When the shaft 40 is not exposed to any external force, or to only a force along its longitudinal central axis, the shaft 40 may retain a straight, linear position as shown.

The one or more fixation members 20 may be described as one or more "tines" having a normally curved position. The tines may be held in a distally extended position within a delivery tool. The distal tips of tines may penetrate the heart tissue to a limited depth before elastically curving back proximally into the normally curved position (shown) upon release from the delivery tool. Further, the fixation members 20 may include one or more aspects described in, for example, U.S. Pat. No. 9,675,579 (Grubac et al.), issued 13 Jun. 2017, and U.S. Pat. No. 9,119,959 (Rys et al.), issued 1 Sep. 2015, each of which is incorporated herein by reference in its entirety.

In some examples, the distal fixation and electrode assembly 36 includes a distal housing-based electrode 22. In the case of using the device 10 as a pacemaker for multiple chamber pacing (e.g., dual or triple chamber pacing) and sensing, the tip electrode 42 may be used as a cathode electrode paired with the proximal housing-based electrode 24 serving as a return anode electrode. Alternatively, the distal housing-based electrode 22 may serve as a return anode electrode paired with tip electrode 42 for sensing ventricular signals and delivering ventricular pacing pulses. In other examples, the distal housing-based electrode 22 may be a cathode electrode for sensing atrial signals and delivering pacing pulses to the atrial myocardium in the target implant region 4. When the distal housing-based electrode 22 serves as an atrial cathode electrode, the proximal housing-based electrode 24 may serve as the return anode paired with the tip electrode 42 for ventricular pacing and sensing and as the return anode paired with the distal housing-based electrode 22 for atrial pacing and sensing.

As shown in this illustration, the target implant region 4 in some pacing applications is along the atrial endocardium 18, generally inferior to the AV node 15 and the His bundle 5. The dart electrode 42 may define the height 47 of the shaft 40 for penetrating through the atrial endocardium 18 in the target implant region 4, through the central fibrous body 16, and into the ventricular myocardium 14 without perforating through the ventricular endocardial surface 17. When the height 47 of the dart electrode 12 is fully advanced into the target implant region 4, the tip electrode 42 may rest within the ventricular myocardium 14, and the distal housing-based electrode 22 may be positioned in intimate contact with or close proximity to the atrial endocardium 18. The dart electrode 12 may have a total combined height 47 of tip electrode 42 and shaft 40 from about 3 mm to about 8 mm in various examples. The diameter of the shaft 40 may be less than about 2 mm, and may be about 1 mm or less, or even about 0.6 mm or less.

The device 10 may include a motion detector 11 within the housing 30. The motion detector 11 may be used to monitor mechanical activity, such as atrial mechanical activity (e.g., an atrial contraction) and/or ventricular mechanical activity (e.g., a ventricular contraction). In some embodiments, the motion detector 11 may be used to detect right atrial mechanical activity. A non-limiting example of a motion detector 11 includes an accelerometer. In some embodiments, the mechanical activity detected by the motion detector 11 may be used to supplement or replace electrical activity detected by one or more of the electrodes of the device 10. For example, the motion detector 11 may be used in addition to, or as an alternative to, the proximal housing-based electrode 24.

The motion detector 11 may also be used for rate response detection or to provide a rate-responsive IMD. Various techniques related to rate response may be described in U.S. Pat. No. 5,154,170 (Bennett et al.), issued Oct. 13, 1992, entitled "Optimization for rate responsive cardiac pacemaker," and U.S. Pat. No. 5,562,711 (Yerich et al.), issued Oct. 8, 1996, entitled "Method and apparatus for rate-responsive cardiac pacing," each of which is incorporated herein by reference in its entirety.

Figure 10:
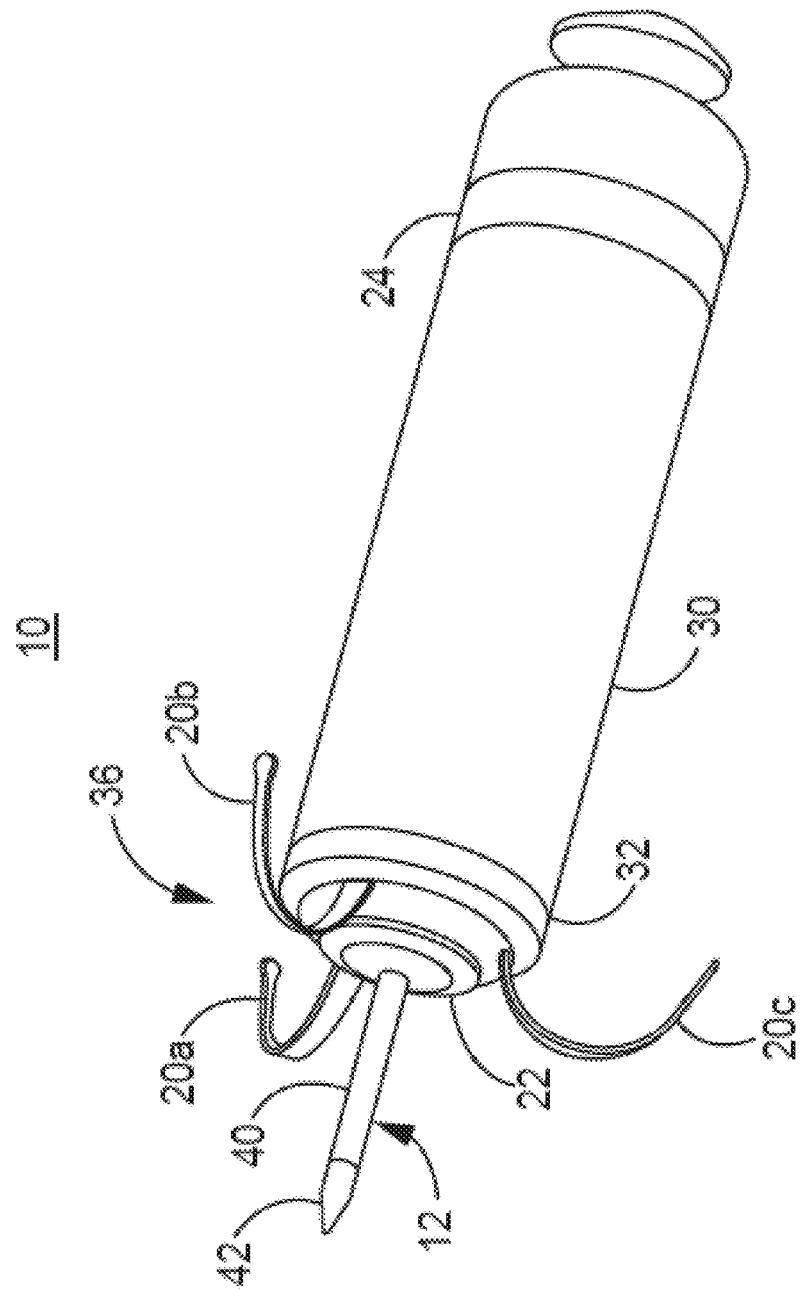
FIG. 10 is a perspective view of the intracardiac medical device of FIGS. 8-9 having a distal fixation and electrode assembly that includes a distal housing-based electrode implemented as a ring electrode.

FIG. 10 is a three-dimensional perspective view of the device 10 capable of cardiac therapy. As shown, the distal fixation and electrode assembly 36 includes the distal housing-based electrode 22 implemented as a ring electrode. The distal housing-based electrode 22 may be positioned in intimate contact with or operative proximity to atrial tissue when fixation member tines 20*a*, 20*b* and 20*c* of the fixation members 20, engage with the atrial tissue. The tines 20*a*, 20*b* and 20*c*, which may be elastically deformable, may be extended distally during delivery of device 10 to the implant site. For example, the tines 20*a*, 20*b*, and 20*c* may pierce the atrial endocardial surface as the device 10 is advanced out of the delivery tool and flex back into their normally curved position (as shown) when no longer constrained within the delivery tool. As the tines 20*a*, 20*b* and 20*c* curve back into their normal position, the fixation member 20 may pull the distal fixation member and electrode assembly 36 toward the atrial endocardial surface. As the distal fixation member and electrode assembly 36 is pulled toward the atrial endocardium, the tip electrode 42 may be advanced through the atrial myocardium and the central fibrous body and into the ventricular myocardium. The distal housing-based electrode 22 may then be positioned against the atrial endocardial surface.

The distal housing-based electrode 22 may include a ring formed of an electrically conductive material, such as titanium, platinum, iridium, or alloys thereof. The distal housing-based electrode 22 may be a single, continuous ring electrode. In other examples, portions of the ring may be coated with an electrically insulating coating, e.g., parylene, polyurethane, silicone, epoxy, or other insulating coating, to reduce the electrically conductive surface area of the ring electrode. For instance, one or more sectors of the ring may be coated to separate two or more electrically conductive exposed surface areas of the distal housing-based electrode 22. Reducing the electrically conductive surface area of the distal housing-based electrode 22, e.g., by covering portions of the electrically conductive ring with an insulating coating, may increase the electrical impedance of the distal housing-based 22, and thereby, reduce the current delivered during a pacing pulse that captures the myocardium, e.g., the atrial myocardial tissue. A lower current drain may conserve the power source, e.g., one or more rechargeable or non-rechargeable batteries, of the device 10.

As described above, the distal housing-based electrode 22 may be configured as an atrial cathode electrode for delivering pacing pulses to the atrial tissue at the implant site in combination with the proximal housing-based electrode 24 as the return anode. The electrodes 22 and 24 may be used to sense atrial P-waves for use in controlling atrial pacing pulses (delivered in the absence of a sensed P-wave) and for controlling atrial-synchronized ventricular pacing pulses delivered using the tip electrode 42 as a cathode and the proximal housing-based electrode 24 as the return anode. In other examples, the distal housing-based electrode 22 may be used as a return anode in conjunction with the cathode tip electrode 42 for ventricular pacing and sensing.

Figure 11:
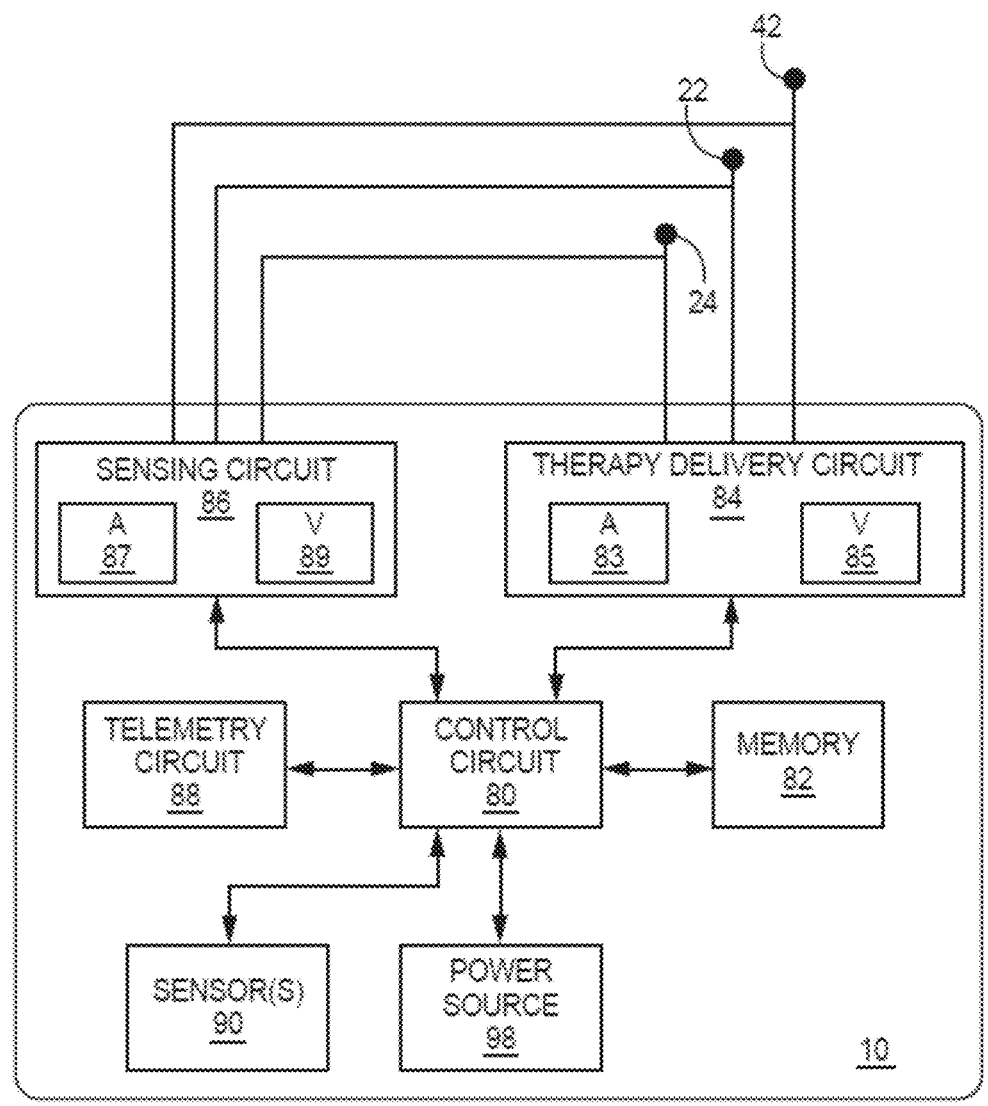
FIG. 11 is a block diagram of illustrative circuitry that may be enclosed within a housing of the intracardiac medical device of FIGS. 8-10, for example, to provide the functionality and therapy described herein.

FIG. 11 is a block diagram of circuitry that may be enclosed within the housing 30 (FIG. 10) to provide the functions of cardiac therapy using the device 10 according to one example. The separate medical device 50 (FIG. 8) may include some or all the same components, which may be configured in a similar manner. The electronic circuitry enclosed within housing 30 may include software, firmware, and hardware that cooperatively monitor atrial and ventricular electrical cardiac signals, determine when a cardiac therapy is necessary, and/or deliver electrical pulses to the patient's heart according to programmed therapy mode and pulse control parameters. The electronic circuitry may include a control circuit 80 (e.g., including processing circuitry), a memory 82, a therapy delivery circuit 84, a sensing circuit 86, and/or a telemetry circuit 88. In some examples, the device 10 includes one or more sensors 90 for producing a signal that is correlated to a physiological function, state, or condition of the patient, such as a patient activity sensor, for use in determining a need for pacing therapy and/or controlling a pacing rate.

The power source 98 may provide power to the circuitry of the device 10 including each of the components 80, 82, 84, 86, 88, and 90 as needed. The power source 98 may include one or more energy storage devices, such as one or more rechargeable or non-rechargeable batteries. The connections between the power source 98 and each of the components 80, 82, 84, 86, 88, and 90 are to be understood from the general block diagram illustrated but are not shown for the sake of clarity. For example, the power source 98 may be coupled to one or more charging circuits included in the therapy delivery circuit 84 for providing the power needed to charge holding capacitors included in the therapy delivery circuit 84 that are discharged at appropriate times under the control of the control circuit 80 for delivering pacing pulses, e.g., according to a dual chamber pacing mode such as DDI(R). The power source 98 may also be coupled to components of the sensing circuit 86, such as sense amplifiers, analog-to-digital converters, switching circuitry, etc., sensors 90, the telemetry circuit 88, and the memory 82 to provide power to the various circuits.

The functional blocks shown represent functionality included in the device 10 and may include any discrete and/or integrated electronic circuit components that implement analog, and/or digital circuits capable of producing the functions attributed to the medical device 10 herein. The various components may include processing circuitry, such as an application specific integrated circuit (ASIC), an electronic circuit, a processor (shared, dedicated, or group), and memory that execute one or more software or firmware programs, a combinational logic circuit, state machine, or other suitable components or combinations of components that provide the described functionality. The particular form of software, hardware, and/or firmware employed to implement the functionality disclosed herein will be determined primarily by the particular system architecture employed in the medical device and by the particular detection and therapy delivery methodologies employed by the medical device. Providing software, hardware, and/or firmware to accomplish the described functionality in the context of any modern cardiac medical device system, given the disclosure herein, is within the abilities of one of skill in the art.

The memory 82 may include any volatile, non-volatile, magnetic, or electrical non-transitory computer readable storage media, such as random-access memory (RAM), read-only memory (ROM), non-volatile RAM (NVRAM), electrically-erasable programmable ROM (EEPROM), flash memory, or any other memory device. Furthermore, the memory 82 may include a non-transitory computer readable media storing instructions that, when executed by one or more processing circuits, cause the control circuit 80 and/or other processing circuitry to perform a single, dual, or triple chamber pacing (e.g., single or multiple chamber pacing) function or other sensing and therapy delivery functions attributed to the device 10. The non-transitory computer-readable media storing the instructions may include any of the media listed above.

The control circuit 80 may communicate, e.g., via a data bus, with the therapy delivery circuit 84 and the sensing circuit 86 for sensing cardiac electrical signals and controlling delivery of cardiac electrical stimulation therapies in response to sensed cardiac events, e.g., P-waves and R-waves, or the absence thereof. The tip electrode 42, the distal housing-based electrode 22, and the proximal housing-based electrode 24 may be electrically coupled to the therapy delivery circuit 84 for delivering electrical stimulation pulses to the patient's heart and to the sensing circuit 86 and for sensing cardiac electrical signals.

The sensing circuit 86 may include an atrial (A) sensing channel 87 and a ventricular (V) sensing channel 89. The distal housing-based electrode 22 and the proximal housing-based electrode 24 may be coupled to the atrial sensing channel 87 for sensing atrial signals, e.g., P-waves attendant to the depolarization of the atrial myocardium. In examples that include two or more selectable distal housing-based electrodes, the sensing circuit 86 may include switching circuitry for selectively coupling one or more of the available distal housing-based electrodes to cardiac event detection circuitry included in the atrial sensing channel 87. Switching circuitry may include a switch array, switch matrix, multiplexer, or any other type of switching device suitable to selectively couple components of the sensing circuit 86 to selected electrodes. The tip electrode 42 and the proximal housing-based electrode 24 may be coupled to the ventricular sensing channel 89 for sensing ventricular signals, e.g., R-waves attendant to the depolarization of the ventricular myocardium.

Each of the atrial sensing channel 87 and the ventricular sensing channel 89 may include cardiac event detection circuitry for detecting P-waves and R-waves, respectively, from the cardiac electrical signals received by the respective sensing channels. The cardiac event detection circuitry included in each of the channels 87 and 89 may be configured to amplify, filter, digitize, and rectify the cardiac electrical signal received from the selected electrodes to improve the signal quality for detecting cardiac electrical events. The cardiac event detection circuitry within each channel 87 and 89 may include one or more sense amplifiers, filters, rectifiers, threshold detectors, comparators, analog-to-digital converters (ADCs), timers, or other analog or digital components. A cardiac event sensing threshold, e.g., a P-wave sensing threshold and an R-wave sensing threshold, may be automatically adjusted by each respective sensing channel 87 and 89 under the control of the control circuit 80, e.g., based on timing intervals and sensing threshold values determined by the control circuit 80, stored in the memory 82, and/or controlled by hardware, firmware, and/or software of the control circuit 80 and/or the sensing circuit 86.

Upon detecting a cardiac electrical event based on a sensing threshold crossing, the sensing circuit 86 may produce a sensed event signal that is passed to the control circuit 80. For example, the atrial sensing channel 87 may produce a P-wave sensed event signal in response to a P-wave sensing threshold crossing. The ventricular sensing channel 89 may produce an R-wave sensed event signal in response to an R-wave sensing threshold crossing. The sensed event signals may be used by the control circuit 80 for setting pacing escape interval timers that control the basic time intervals used for scheduling cardiac pacing pulses. A sensed event signal may trigger or inhibit a pacing pulse depending on the particular programmed pacing mode. For example, a P-wave sensed event signal received from the atrial sensing channel 87 may cause the control circuit 80 to inhibit a scheduled atrial pacing pulse and schedule a ventricular pacing pulse at a programmed atrioventricular (AV) pacing interval. If an R-wave is sensed before the AV pacing interval expires, the ventricular pacing pulse may be inhibited. If the AV pacing interval expires before the control circuit 80 receives an R-wave sensed event signal from the ventricular sensing channel 89, the control circuit 80 may use the therapy delivery circuit 84 to deliver the scheduled ventricular pacing pulse synchronized to the sensed P-wave.

In some examples, the device 10 may be configured to deliver a variety of pacing therapies including bradycardia pacing, cardiac resynchronization therapy, post-shock pacing, and/or tachycardia-related therapy, such as ATP, among others. For example, the device 10 may be configured to detect non-sinus tachycardia and deliver ATP. The control circuit 80 may determine cardiac event time intervals, e.g., PP intervals between consecutive P-wave sensed event signals received from the atrial sensing channel 87, RR intervals between consecutive R-wave sensed event signals received from the ventricular sensing channel 89, and P-R and/or R-P intervals received between P-wave sensed event signals and R-wave sensed event signals. These intervals may be compared to tachycardia detection intervals for detecting non-sinus tachycardia. Tachycardia may be detected in a given heart chamber based on a threshold number of tachycardia detection intervals being detected.

The therapy delivery circuit 84 may include atrial pacing circuit 83 and ventricular pacing circuit 85. Each pacing circuit 83 and 85 may include charging circuitry, one or more charge storage devices such as one or more low voltage holding capacitors, an output capacitor, and/or switching circuitry that controls when the holding capacitor(s) are charged and discharged across the output capacitor to deliver a pacing pulse to the pacing electrode vector coupled to respective pacing circuits 83 or 85. The tip electrode 42 and the proximal housing-based electrode 24 may be coupled to the ventricular pacing circuit 85 as a bipolar cathode and anode pair for delivering ventricular pacing pulses, e.g., upon expiration of an AV or VV pacing interval set by the control circuit 80 for providing atrial-synchronized ventricular pacing and a basic lower ventricular pacing rate.

The atrial pacing circuit 83 may be coupled to the distal housing-based electrode 22 and the proximal housing-based electrode 24 to deliver atrial pacing pulses. The control circuit 80 may set atrial pacing intervals according to a programmed lower pacing rate or a temporary lower rate set according to a rate-responsive sensor indicated pacing rate. Atrial pacing circuit may be controlled to deliver an atrial pacing pulse if the atrial pacing interval expires before a P-wave sensed event signal is received from the atrial sensing channel 87. The control circuit 80 starts an AV pacing interval in response to a delivered atrial pacing pulse to provide synchronized multiple chamber pacing (e.g., dual or triple chamber pacing).

Charging of a holding capacitor of the atrial or ventricular pacing circuit 83 or 85 to a programmed pacing voltage amplitude and discharging of the capacitor for a programmed pacing pulse width may be performed by the therapy delivery circuit 84 according to control signals received from the control circuit 80. For example, a pace timing circuit included in the control circuit 80 may include programmable digital counters set by a microprocessor of the control circuit 80 for controlling the basic pacing time intervals associated with various single chamber or multiple chamber pacing (e.g., dual or triple chamber pacing) modes or anti-tachycardia pacing sequences. The microprocessor of the control circuit 80 may also set the amplitude, pulse width, polarity, or other characteristics of the cardiac pacing pulses, which may be based on programmed values stored in the memory 82.

The device 10 may include other sensors 90 for sensing signals from the patient for use in determining a need for and/or controlling electrical stimulation therapies delivered by the therapy delivery circuit 84. In some examples, a sensor indicative of a need for increased cardiac output may include a patient activity sensor, such as an accelerometer. An increase in the metabolic demand of the patient due to increased activity as indicated by the patient activity sensor may be determined by the control circuit 80 for use in determining a sensor-indicated pacing rate.

Control parameters utilized by the control circuit 80 for sensing cardiac events and controlling pacing therapy delivery may be programmed into the memory 82 via the telemetry circuit 88, which may also be described as a communication interface. The telemetry circuit 88 includes a transceiver and antenna for communicating with an external device such as a programmer or home monitor, using radio frequency communication or other communication protocols. The control circuit 80 may use the telemetry circuit 88 to receive downlink telemetry from and send uplink telemetry to the external device. In some cases, the telemetry circuit 88 may be used to transmit and receive communication signals to/from another medical device implanted in the patient.

Figure 12:
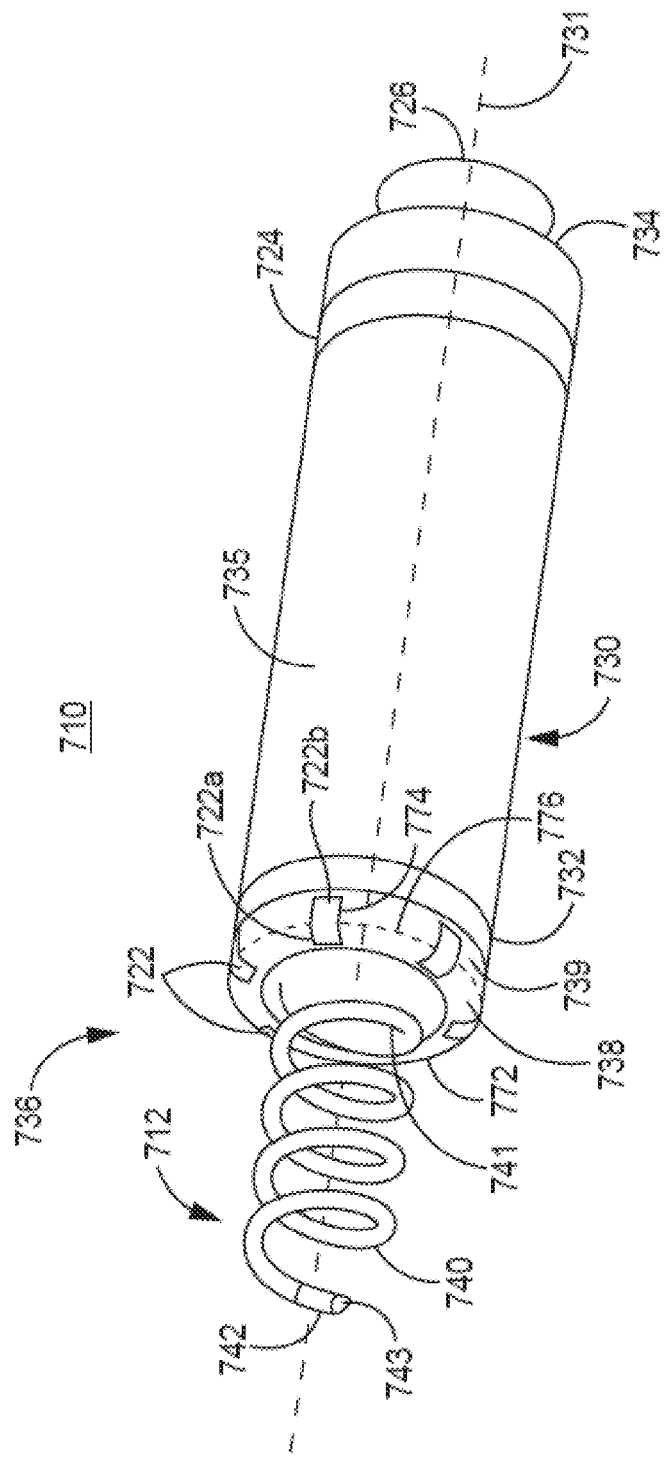
FIG. 12 is a perspective view of an exemplary intracardiac medical device according to another example for use with, e.g., the exemplary system of FIG. 8.

FIG. 12 is a three-dimensional perspective view of another leadless intracardiac medical device 710 that may be configured for single or multiple chamber cardiac therapy (e.g., dual or triple chamber cardiac therapy) according to another example. The device 710 may include a housing 730 having an outer sidewall 735, shown as a cylindrical outer sidewall, extending from a housing distal end region 732 to a housing proximal end region 734. The housing 730 may enclose electronic circuitry configured to perform single or multiple chamber cardiac therapy, including atrial and ventricular cardiac electrical signal sensing and pacing the atrial and ventricular chambers. Delivery tool interface member 726 is shown on the housing proximal end region 734.

A distal fixation and electrode assembly 736 may be coupled to the housing distal end region 732. The distal fixation and electrode assembly 736 may include an electrically insulative distal member 772 coupled to the housing distal end region 732. The tissue piercing electrode 712 extends away from the housing distal end region 732, and multiple non-tissue piercing electrodes 722 may be coupled directly to the insulative distal member 772. The tissue piercing electrode 712 extends in a longitudinal direction away from the housing distal end region 732 and may be coaxial with the longitudinal center axis 731 of the housing 730.

The tissue piercing distal electrode 712 may include an electrically insulated shaft 740 and a tip electrode 742. In some examples, the tissue piercing distal electrode 712 is an active fixation member including a helical shaft 740 and a distal cathode tip electrode 742. The helical shaft 740 may extend from a shaft distal end region 743 to a shaft proximal end region 741, which may be directly coupled to the insulative distal member 772. The helical shaft 740 may be coated with an electrically insulating material, e.g., parylene or other examples listed herein, to avoid sensing or stimulation of cardiac tissue along the shaft length. The tip electrode 742 is at the shaft distal end region 743 and may serve as a cathode electrode for delivering ventricular pacing pulses and sensing ventricular electrical signals using the proximal housing-based electrode 724 as a return anode when the tip electrode 742 is advanced into ventricular tissue. The proximal housing-based electrode 724 may be a ring electrode circumscribing the housing 730 and may be defined by an uninsulated portion of the longitudinal sidewall 735. Other portions of the housing 730 not serving as an electrode may be coated with an electrically insulating material as described above in conjunction with FIG. 9.

Using two or more tissue-piercing electrodes (e.g., of any type) penetrating into the LV myocardium may be used for more localized pacing capture and may mitigate ventricular pacing spikes affecting capturing atrial tissue. In some embodiments, multiple tissue-piercing electrodes may include two or more of a dart-type electrode (e.g., electrode 12 of FIGS. 8-9), a helical-type electrode (e.g., electrode 712) Non-limiting examples of multiple tissue-piercing electrodes include two dart electrodes, a helix electrode with a dart electrode extending therethrough (e.g., through the center), or dual intertwined helixes. Multiple tissue-piercing electrodes may also be used for bipolar or multi-polar pacing.

In some embodiments, one or more tissue-piercing electrodes (e.g., of any type) that penetrate into the LV myocardium may be a multi-polar tissue-piercing electrode. A multi-polar tissue-piercing electrode may include one or more electrically active and electrically separate elements, which may enable bipolar or multi-polar pacing from one or more tissue-piercing electrodes.

Multiple non-tissue piercing electrodes 722 may be provided along a periphery of the insulative distal member 772, peripheral to the tissue piercing electrode 712. The insulative distal member 772 may define a distal-facing surface 738 of the device 710 and a circumferential surface 739 that circumscribes the device 710 adjacent to the housing longitudinal sidewall 735. Non-tissue piercing electrodes 722 may be formed of an electrically conductive material, such as titanium, platinum, iridium, or alloys thereof. In the illustrated embodiment, six non-tissue piercing electrodes 722 are spaced apart radially at equal distances along the outer periphery of insulative distal member 772, however, two or more non-tissue piercing electrodes 722 may be provided.

Non-tissue piercing electrodes 722 may be discrete components each retained within a respective recess 774 in the insulative member 772 sized and shaped to mate with the non-tissue piercing electrode 722. In other examples, the non-tissue piercing electrodes 722 may each be an uninsulated, exposed portion of a unitary member mounted within or on the insulative distal member 772. Intervening portions of the unitary member not functioning as an electrode may be insulated by the insulative distal member 772 or, if exposed to the surrounding environment, may be coated with an electrically insulating coating, e.g., parylene, polyurethane, silicone, epoxy, or other insulating coating.

When the tissue piercing electrode 712 is advanced into cardiac tissue, at least one non-tissue piercing electrode 722 may be positioned against, in intimate contact with, or in operative proximity to, a cardiac tissue surface for delivering pulses and/or sensing cardiac electrical signals produced by the patient's heart. For example, non-tissue piercing electrodes 722 may be positioned in contact with right atrial endocardial tissue for pacing and sensing in the atrium when the tissue piercing electrode 712 is advanced into the atrial tissue and through the central fibrous body until the distal tip electrode 742 is positioned in direct contact with ventricular tissue, e.g., ventricular myocardium and/or a portion of the ventricular conduction system.

Non-tissue piercing electrodes 722 may be coupled to the therapy delivery circuit 84 and the sensing circuit 86 (see FIG. 11) enclosed by the housing 730 to function collectively as a cathode electrode for delivering atrial pacing pulses and for sensing atrial electrical signals, e.g., P-waves, in combination with the proximal housing-based electrode 724 as a return anode. Switching circuitry included in the sensing circuit 86 may be activated under the control of the control circuit 80 to couple one or more of the non-tissue piercing electrodes to the atrial sensing channel 87. Distal, non-tissue piercing electrodes 722 may be electrically isolated from each other so that each individual one of the electrodes 722 may be individually selected by switching circuitry included in the therapy delivery circuit 84 to serve alone or in a combination of two or more of the electrodes 722 as an atrial cathode electrode. Switching circuitry included in the therapy delivery circuit 84 may be activated under the control of the control circuit 80 to couple one or more of the non-tissue piercing electrodes 722 to the atrial pacing circuit 83. Two or more of the non-tissue piercing electrodes 722 may be selected at a time to operate as a multi-point atrial cathode electrode.

Certain non-tissue piercing electrodes 722 selected for atrial pacing and/or atrial sensing may be selected based on atrial capture threshold tests, electrode impedance, P-wave signal strength in the cardiac electrical signal, or other factors. For example, a single one or any combination of two or more individual non-tissue piercing electrodes 722 functioning as a cathode electrode that provides an optimal combination of a low pacing capture threshold amplitude and relatively high electrode impedance may be selected to achieve reliable atrial pacing using minimal current drain from the power source 98.

In some instances, the distal-facing surface 738 may uniformly contact the atrial endocardial surface when the tissue piercing electrode 712 anchors the housing 730 at the implant site. In that case, all the electrodes 722 may be selected together to form the atrial cathode. Alternatively, every other one of the electrodes 722 may be selected together to form a multi-point atrial cathode having a higher electrical impedance that is still uniformly distributed along the distal-facing surface 738. Alternatively, a subset of one or more electrodes 722 along one side of the insulative distal member 772 may be selected to provide pacing at a desired site that achieves the lowest pacing capture threshold due to the relative location of the electrodes 722 to the atrial tissue being paced.

In other instances, the distal-facing surface 738 may be oriented at an angle relative to the adjacent endocardial surface depending on the positioning and orientation at which the tissue piercing electrode 712 enters the cardiac tissue. In this situation, one or more of the non-tissue piercing electrodes 722 may be positioned in closer contact with the adjacent endocardial tissue than other non-tissue piercing electrodes 722, which may be angled away from the endocardial surface. By providing multiple non-tissue piercing electrodes along the periphery of the insulative distal member 772, the angle of the tissue piercing electrode 712 and the housing distal end region 732 relative to the cardiac surface, e.g., the right atrial endocardial surface, may not be required to be substantially parallel. Anatomical and positional differences may cause the distal-facing surface 738 to be angled or oblique to the endocardial surface, however, multiple non-tissue piercing electrodes 722 distributed along the periphery of the insulative distal member 772 increase the likelihood of good contact between one or more electrodes 722 and the adjacent cardiac tissue to promote acceptable pacing thresholds and reliable cardiac event sensing using at least a subset of multiple electrodes 722. Contact or fixation circumferentially along the entire periphery of the insulative distal member 772 may not be required.

The non-tissue piercing electrodes 722 are shown to each include a first portion 722a extending along the distal-facing surface 738 and a second portion 722b extending along the circumferential surface 739. The first portion 722a and the second portion 722b may be continuous exposed surfaces such that the active electrode surface wraps around a peripheral edge 776 of the insulative distal member 772 that joins the distal facing surface 738 and the circumferential surface 739. The non-tissue piercing electrodes 722 may include one or more of the electrodes 772 along the distal-facing surface 738, one or more electrodes along the circumferential surface 739, one or more electrodes each extending along both of the distal-facing surface 738 and the circumferential surface 739, or any combination thereof. The exposed surface of each of the non-tissue piercing electrodes 722 may be flush with respective distal-facing surfaces 738 and/or circumferential surfaces. In other examples, each of the non-tissue piercing electrodes 722 may have a raised surface that protrudes from the insulative distal member 772. Any raised surface of the electrodes 722, however, may define a smooth or rounded, non-tissue piercing surface.

The distal fixation and electrode assembly 736 may seal the distal end region of the housing 730 and may provide a foundation on which the electrodes 722 are mounted. The electrodes 722 may be referred to as housing-based electrodes. The electrodes 722 may not be not carried by a shaft or other extension that extends the active electrode portion away from the housing 730, like the distal tip electrode 742 residing at the distal tip of the helical shaft 740 extending away from the housing 730. Other examples of non-tissue piercing electrodes presented herein that are coupled to a distal-facing surface and/or a circumferential surface of an insulative distal member include the distal housing-based ring electrode 22 (FIG. 10), the distal housing-based ring electrode extending circumferentially around the assembly 36 (FIG. 10), button electrodes, other housing-based electrodes, and other circumferential ring electrodes. Any non-tissue piercing electrodes directly coupled to a distal insulative member, peripherally to a central tissue-piercing electrode, may be provided to function individually, collectively, or in any combination as a cathode electrode for delivering pacing pulses to adjacent cardiac tissue. When a ring electrode, such as the distal ring electrode 22 and/or a circumferential ring electrode, is provided, portions of the ring electrode may be electrically insulated by a coating to provide multiple distributed non-tissue piercing electrodes along the distal-facing surface and/or the circumferential surface of the insulative distal member.

The non-tissue piercing electrodes 722 and other examples listed above are expected to provide more reliable and effective atrial pacing and sensing than a tissue piercing electrode provided along the distal fixation and electrode assembly 736. The atrial chamber walls are relatively thin compared to ventricular chamber walls. A tissue piercing atrial cathode electrode may extend too deep within the atrial tissue leading to inadvertent sustained or intermittent capture of ventricular tissue. A tissue piercing atrial cathode electrode may lead to interference with sensing atrial signals due to ventricular signals having a larger signal strength in the cardiac electrical signal received via tissue-piercing atrial cathode electrodes that are in closer physical proximity to the ventricular tissue. The tissue piercing electrode 712 may be securely anchored into ventricular tissue for stabilizing the implant position of the device 710 and providing reasonable certainty that the tip electrode 742 is sensing and pacing in ventricular tissue while the non-tissue piercing electrodes 722 are reliably pacing and sensing in the atrium. When the device 710 is implanted in the target implant region 4, e.g., as shown in FIG. 8 the ventricular septum, the tip electrode 742 may reach left ventricular tissue for pacing of the left ventricle while the non-tissue piercing electrodes 722 provide pacing and sensing in the right atrium. The tissue piercing electrode 712 may be in the range of about 4 to about 8 mm in length from the distal-facing surface 738 to reach left ventricular tissue. In some instances, the device 710 may achieve four-chamber pacing by delivering atrial pacing pulses from the atrial pacing circuit 83 via the non-tissue piercing electrodes 722 in the target implant region 4 to achieve bi-atrial (right and left atrial) capture and by delivering ventricular pacing pulses from the ventricular pacing circuit 85 via the tip electrode 742 advanced into ventricular tissue from the target implant region 4 to achieve biventricular (right and left ventricular) capture.

Figure 13:
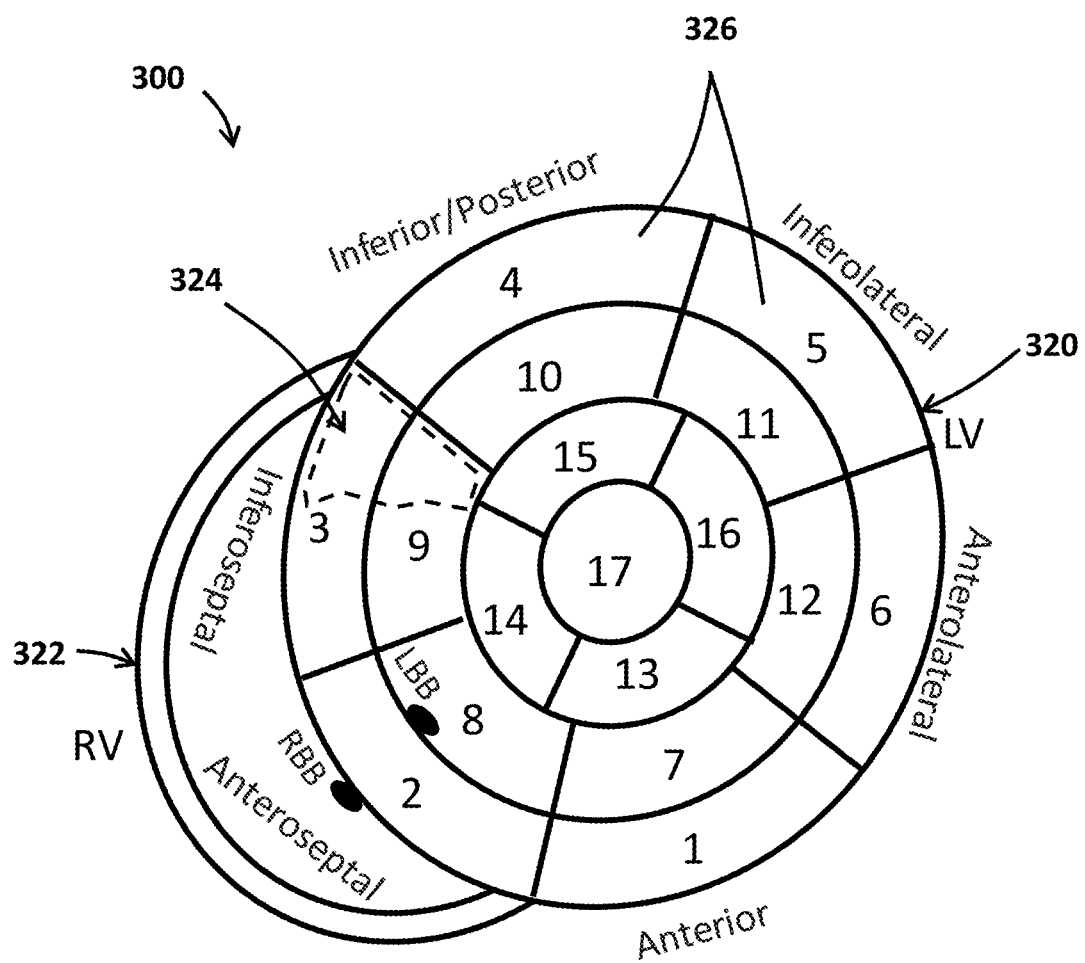
FIG. 13 is a conceptual diagram of a map of a patient's heart in a standard seventeen (17) segment view of the left ventricle showing various electrode implantation locations for use with, e.g., the exemplary system and devices of FIGS. 8-12.

FIG. 13 is a two-dimensional (2D) ventricular map 300 of a patient's heart (e.g., a top-down view) showing the left ventricle 320 in a standard 17 segment view and the right ventricle 322. The map 300 includes a plurality of areas 326 corresponding to different regions of a human heart. As illustrated, the areas 326 are numerically labeled 1-17 (which, e.g., correspond to a standard 17 segment model of a human heart, correspond to 17 segments of the left ventricle of a human heart, etc.). Areas 326 of the map 300 may include basal anterior area 1, basal anteroseptal area 2, basal inferoseptal area 3, basal inferior area 4, basal inferolateral area 5, basal anterolateral area 6, mid-anterior area 7, mid-anteroseptal area 8, mid-inferoseptal area 9, mid-inferior area 10, mid-inferolateral area 11, mid-anterolateral area 12, apical anterior area 13, apical septal area 14, apical inferior area 15, apical lateral area 16, and apex area 17. The inferoseptal and anteroseptal areas of the right ventricle 322 are also illustrated, as well as the right bunch branch (RBB) and left bundle branch (LBB).

In some embodiments, any of the tissue-piercing electrodes of the present disclosure may be implanted through the right atrial endocardium. In particular, the tissue-piercing electrode may be implanted from the triangle of Koch region of the right atrium.

Once implanted, the tissue-piercing electrode may be positioned in the target implant region 4 (FIG. 8), such as the basal and/or septal region of the left ventricular myocardium. With reference to map 300, the basal region includes one or more of the basal anterior area 1, basal anteroseptal area 2, basal inferoseptal area 3, basal inferior area 4, mid-anterior area 7, mid-anteroseptal area 8, mid-inferoseptal area 9, and mid-inferior area 10. With reference to map 300, the septal region includes one or more of the basal anteroseptal area 2, basal anteroseptal area 3, mid-anteroseptal area 8, mid-inferoseptal area 9, and apical septal area 14.

In some embodiments, the tissue-piercing electrode may be positioned in the basal and/or septal area of the left ventricular myocardium when implanted. The basal and/or septal region may include one or more of the basal anteroseptal area 2, basal inferoseptal area 3, mid-anteroseptal area 8, and mid-inferoseptal area 9.

In some embodiments, the tissue-piercing electrode may be positioned in the basal and/or septal region of the left ventricular myocardium when implanted. The high inferior/posterior basal and/or septal region of the left ventricular myocardium may include a portion of at least one of the basal inferoseptal area 3 and mid-inferoseptal area 9. For example, the high inferior/posterior basal and/or septal region may include region 324 illustrated generally as a dashed-line boundary. As shown, the dashed line boundary represents an approximation of about where the high inferior/posterior basal and/or septal region and may take somewhat different shape or size depending on the particular application.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

ILLUSTRATIVE EMBODIMENTS

Embodiment 1

A system comprising:
electrode apparatus comprising a plurality of external electrodes to monitor electrical activity from tissue of a patient; and
computing apparatus comprising processing circuitry and coupled to the electrode apparatus and configured to:
monitor electrical activity using the plurality of external electrodes;
generate paced electrical heterogeneity information (EHI) based on the monitored electrical activity during delivery of ventricle from atrium (VfA) pacing therapy at one or more VfA paced settings, wherein the paced EHI is representative of at least one of mechanical cardiac functionality and electrical cardiac functionality; and
determine whether the one or more VfA paced settings for the VfA pacing therapy are acceptable based on the paced EHI.

Embodiment 2

The system of embodiment 1, wherein the one or more VfA paced settings comprise at least one of a voltage, a pulse width, timing of a V-pacing relative to intrinsic or paced atrial timing, and pacing rate.

Embodiment 3

The system of any one of embodiments 1 to 2, wherein the one or more VfA paced settings comprises a location of at least one implantable electrode wherein the location comprises at least one of depth and angle.

Embodiment 4

The system of any one of embodiments 1 to 3, wherein the one or more VfA paced settings comprises at least one of a pacing polarity, a pacing vector, and a number of pacing electrodes used.

Embodiment 5

The system of any one of embodiments 1 to 4, wherein the system further comprises a VfA pacing therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient's heart.

Embodiment 6

The system of any one of embodiments 1 to 5, wherein the VfA paced settings comprises a location of the at least one implantable electrode proximate the high posterior basal and/or septal area of the left ventricle of the patient.

Embodiment 7

The system of any one of embodiments 1 to 6, wherein the plurality of external electrodes comprises surface electrodes positioned in an array configured to be located proximate skin of a torso of the patient.

Embodiment 8

The system of any one of embodiments 1 to 7, wherein the paced EHI comprises a metric of electrical heterogeneity, wherein the determining whether the one or more VfA paced settings for the VfA pacing therapy are acceptable comprises determining that the one or more VfA paced settings are acceptable if the metric of electrical heterogeneity is less than or equal to a threshold.

Embodiment 9

The system of any one of embodiments 1 to 8, wherein the determining whether the one or more VfA paced settings for the VfA pacing therapy are acceptable comprises:
generating baseline EHI from the monitored electrical activity without delivery of the VfA pacing therapy;
comparing the baseline EHI to the paced EHI; and
determining that the one or more VfA paced settings are acceptable based on the comparison of the baseline EHI to the paced EHI.

Embodiment 10

The system of any one of embodiments 1 to 9, wherein the electrical heterogeneity information comprises at least one metric of electrical heterogeneity, wherein the at least one metric of electrical heterogeneity comprises anterior-septal activation times (ASAT), wherein ASAT comprises activation times monitored from external electrodes of the plurality of external electrodes that correspond to the anterior-septal region of the heart of the patient.

Embodiment 11

The system of any one of embodiments 1 to 10, wherein the electrical heterogeneity information comprises at least one metric of electrical heterogeneity, wherein the at least one metric of electrical heterogeneity comprises at least one of anterior-septal activation times (ASAT), a standard deviation of activation times (SDAT), a composite left ventricular activation time (LVAT), and a composite right ventricular activation time (RVAT).

Embodiment 12

The system of any one of embodiments 1 to 11, wherein the computing apparatus is further configured to adjust the one or more VfA paced settings for the VfA pacing therapy based on whether the VfA pacing therapy is acceptable; and wherein the adjusted one or more VfA paced settings is determined to be acceptable in response to the VfA pacing therapy correcting a bundle branch block (BBB).

Embodiment 13

The system of any one of embodiments 1 to 12, wherein the computing apparatus is further configured to adjust the one or more VfA paced settings for the VfA pacing therapy based on whether the VfA pacing therapy is acceptable; and wherein the adjusted one or more VfA paced settings is determined to be acceptable in response to the VfA pacing therapy completely engaging a Purkinje system of the heart of the patient.

Embodiment 14

A method comprising:
monitoring electrical activity from tissue of a patient using a plurality of external electrodes;
generating paced electrical heterogeneity information (EHI) based on the monitored electrical activity during delivery of ventricle from atrium (VfA) pacing therapy at one or more VfA paced settings, wherein the paced EHI is representative of at least one of mechanical cardiac functionality and electrical cardiac functionality; and
determining whether the one or more VfA paced settings for the VfA pacing therapy are acceptable based on the paced EHI.

Embodiment 15

The method of embodiment 14, wherein the one or more VfA paced settings comprise at least one of a voltage, a pulse width, timing of a V-pacing relative to intrinsic or paced atrial timing, and pacing rate.

Embodiment 16

The method of any one of embodiments 14 to 15, wherein the one or more VfA paced settings comprises a location of at least one implantable electrode wherein the location comprises at least one of depth and angle.

Embodiment 17

The method of any one of embodiments 14 to 16, wherein the one or more VfA paced settings comprises at least one of a pacing polarity, a pacing vector, and a number of pacing electrodes used.

Embodiment 18

The method of any one of embodiments 14 to 17, wherein the delivery of the VfA pacing therapy is performed by a VfA therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient.

Embodiment 19

The method of embodiment 18, wherein the VfA paced settings comprises a location of the at least one implantable electrode proximate the high posterior basal and/or septal area of the left ventricle of the patient.

Embodiment 20

The method of any one of embodiments 14 to 19, wherein the plurality of external electrodes comprises surface electrodes positioned in an array configured to be located proximate skin of a torso of the patient.

Embodiment 21

The method of any one of embodiments 14 to 20, wherein the paced EHI comprises a metric of electrical heterogeneity, wherein the determining whether the one or more VfA paced settings for the VfA pacing therapy are acceptable comprises determining that the one or more VfA paced settings are acceptable if the metric of electrical heterogeneity is less than or equal to a threshold.

Embodiment 22

The method of any one of embodiments 14 to 21, wherein the determining whether the one or more VfA paced settings for the VfA pacing therapy are acceptable comprises:
generating baseline EHI from the monitored electrical activity without delivery of the VfA pacing therapy;
comparing the baseline EHI to the paced EHI; and
determining that the one or more VfA paced settings are acceptable based on the comparison of the baseline EHI to the paced EHI.

Embodiment 23

The method of any one of embodiments 14 to 22, wherein the electrical heterogeneity information comprises at least one metric of electrical heterogeneity, wherein the at least one metric of electrical heterogeneity comprises anterior-septal activation times (ASAT), wherein ASAT comprises activation times monitored from external electrodes of the plurality of external electrodes that correspond to the anterior-septal region of the heart of the patient.

Embodiment 24

The method of any one of embodiments 14 to 23, wherein the electrical heterogeneity information comprises at least one metric of electrical heterogeneity, wherein the at least one metric of electrical heterogeneity comprises at least one of anterior-septal activation times (ASAT), a standard deviation of activation times (SDAT), a composite left ventricular activation time (LVAT), and a composite right ventricular activation time (RVAT).

Embodiment 25

The method of any one of embodiments 14 to 24, further comprising adjusting the one or more VfA paced settings for the VfA pacing therapy based on whether the VfA pacing therapy is acceptable; and wherein the adjusted one or more VfA paced settings is determined to be acceptable in response to the VfA pacing therapy correcting a bundle branch block (BBB).

Embodiment 26

The method of any one of embodiments 14 to 26, wherein the computing apparatus is further configured to adjust the one or more VfA paced settings for the VfA pacing therapy based on whether the VfA pacing therapy is acceptable; and wherein the adjusted one or more VfA paced settings is determined to be acceptable in response to the VfA pacing therapy completely engaging a Purkinje system of the heart of the patient.

Embodiment 27

A system comprising:

electrode apparatus comprising a plurality of external electrodes to monitor electrical activity from tissue of a patient; and computing apparatus comprising processing circuitry and coupled to the electrode apparatus and configured to:
monitor electrical activity using the plurality of external electrodes during delivery of ventricle from atrium (VfA) pacing therapy;
generate electrical heterogeneity information (EHI) during delivery of VfA pacing therapy;
determine whether a VfA paced setting for the VfA pacing therapy is acceptable based on the EHI generated from the electrical activity using the VfA paced setting; and
adjust the paced setting for the VfA pacing therapy based on whether the VfA pacing therapy is acceptable.

What is claimed:

1. A system comprising:
electrode apparatus comprising a plurality of external electrodes to monitor electrical activity from tissue of a patient and
computing apparatus comprising processing circuitry and coupled to the electrode apparatus and configured to:
monitor electrical activity using the plurality of external electrodes;
generate paced electrical heterogeneity information (EHI) based on the monitored electrical activity during delivery of ventricle from atrium (VfA) pacing therapy at one or more VfA paced settings, wherein the paced EHI is representative of at least one of mechanical cardiac functionality and electrical cardiac functionality; and
determine whether the one or more VfA paced settings for the VfA pacing therapy are acceptable based on the paced EHI.

2. The system of claim 1, wherein the one or more VfA paced settings comprise at least one of a voltage, a pulse width, timing of a V-pacing relative to intrinsic or paced atrial timing, and pacing rate.

3. The system of claim 1, wherein the one or more VfA paced settings comprises a location of at least one implantable electrode wherein the location comprises at least one of depth and angle.

4. The system of claim 1, wherein the one or more VfA paced settings comprises at least one of a pacing polarity, a pacing vector, and a number of pacing electrodes used.

5. The system of claim 1, wherein the system further comprises a VfA pacing therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient's heart.

6. The system of claim 5, wherein the VfA paced settings comprises a location of the at least one implantable electrode proximate the high posterior basal and/or septal area of the left ventricle of the patient.

7. The system of claim 1, wherein the plurality of external electrodes comprises surface electrodes positioned in an array configured to be located proximate skin of a torso of the patient.

8. The system of claim 1, wherein the paced EHI comprises a metric of electrical heterogeneity,
wherein the determining whether the one or more VfA paced settings for the VfA pacing therapy are acceptable comprises determining that the one or more VfA paced settings are acceptable if the metric of electrical heterogeneity is less than or equal to a threshold.

9. The system of claim 1, wherein the determining whether the one or more VfA paced settings for the VfA pacing therapy are acceptable comprises:
generating baseline EHI from the monitored electrical activity without delivery of the VfA pacing therapy;
comparing the baseline EHI to the paced EHI; and
determining that the one or more VfA paced settings are acceptable based on the comparison of the baseline EHI to the paced EHI.

10. The system of claim 1, wherein the electrical heterogeneity information comprises at least one metric of electrical heterogeneity, wherein the at least one metric of electrical heterogeneity comprises anterior-septal activation times (ASAT), wherein ASAT comprises activation times monitored from external electrodes of the plurality of external electrodes that correspond to the anterior-septal region of the heart of the patient.

11. The system of claim 1, wherein the electrical heterogeneity information comprises at least one metric of electrical heterogeneity, wherein the at least one metric of electrical heterogeneity comprises at least one of anterior-septal activation times (ASAT), a standard deviation of activation times (SDAT), a composite left ventricular activation time (LVAT), and a composite right ventricular activation time (RVAT).

12. The system of claim 1, wherein the computing apparatus is further configured to adjust the one or more VfA paced settings for the VfA pacing therapy based on whether the VfA pacing therapy is acceptable; and
wherein the adjusted one or more VfA paced settings is determined to be acceptable in response to the VfA pacing therapy correcting a bundle branch block (BBB).

13. The system of claim 1, wherein the computing apparatus is further configured to adjust the one or more VfA paced settings for the VfA pacing therapy based on whether the VfA pacing therapy is acceptable; and
wherein the adjusted one or more VfA paced settings is determined to be acceptable in response to the VfA pacing therapy completely engaging a Purkinje system of the heart of the patient.

14. A method comprising:
monitoring electrical activity from tissue of a patient using a plurality of external electrodes;
generating paced electrical heterogeneity information (EHI) based on the monitored electrical activity during delivery of ventricle from atrium (VfA) pacing therapy at one or more VfA paced settings, wherein the paced EHI is representative of at least one of mechanical cardiac functionality and electrical cardiac functionality; and
determining whether the one or more VfA paced settings for the VfA pacing therapy are acceptable based on the paced EHI.

15. The method of claim 14, wherein the one or more VfA paced settings comprise at least one of a voltage, a pulse width, timing of a V-pacing relative to intrinsic or paced atrial timing, and pacing rate.

16. The method of claim 14, wherein the one or more VfA paced settings comprises a location of at least one implantable electrode wherein the location comprises at least one of depth and angle.

17. The method of claim 14, wherein the one or more VfA paced settings comprises at least one of a pacing polarity, a pacing vector, and a number of pacing electrodes used.

18. The method of claim 14, wherein the delivery of the VfA pacing therapy is performed by a VfA pacing therapy apparatus, wherein the VfA pacing therapy apparatus comprises a tissue-piercing electrode implantable from the triangle of Koch region of the right atrium through the right atrial endocardium and central fibrous body to deliver the VfA pacing therapy to the left ventricle in the basal and/or septal region of the left ventricular myocardium of the patient.

19. The method of claim 18, wherein the VfA paced settings comprises a location of the at least one implantable electrode proximate the high posterior basal and/or septal area of the left ventricle of the patient.

20. The method of claim 14, wherein the plurality of external electrodes comprises surface electrodes positioned in an array configured to be located proximate skin of a torso of the patient.

21. The method of claim 14, wherein the paced EHI comprises a metric of electrical heterogeneity,
wherein the determining whether the one or more VfA paced settings for the VfA pacing therapy are acceptable comprises determining that the one or more VfA paced settings are acceptable if the metric of electrical heterogeneity is less than or equal to a threshold.

22. The method of claim 14, wherein the determining whether the one or more VfA paced settings for the VfA pacing therapy are acceptable comprises:
generating baseline EHI from the monitored electrical activity without delivery of the VfA pacing therapy;
comparing the baseline EHI to the paced EHI; and
determining that the one or more VfA paced settings are acceptable based on the comparison of the baseline EHI to the paced EHI.

23. The method of claim 14, wherein the electrical heterogeneity information comprises at least one metric of electrical heterogeneity, wherein the at least one metric of electrical heterogeneity comprises anterior-septal activation times (ASAT), wherein ASAT comprises activation times monitored from external electrodes of the plurality of external electrodes that correspond to the anterior-septal region of the heart of the patient.

24. The method of claim 14, wherein the electrical heterogeneity information comprises at least one metric of electrical heterogeneity, wherein the at least one metric of electrical heterogeneity comprises at least one of anterior-septal activation times (ASAT), a standard deviation of activation times (SDAT), a composite left ventricular activation time (LVAT), and a composite right ventricular activation time (RVAT).

25. The method of claim 14, further comprising adjusting the one or more VfA paced settings for the VfA pacing therapy based on whether the VfA pacing therapy is acceptable; and
wherein the adjusted one or more VfA paced settings is determined to be acceptable in response to the VfA pacing therapy correcting a bundle branch block (BBB).

26. The method of claim 14, wherein the computing apparatus is further configured to adjust the one or more VfA paced settings for the VfA pacing therapy based on whether the VfA pacing therapy is acceptable; and
wherein the adjusted one or more VfA paced settings is determined to be acceptable in response to the VfA pacing therapy completely engaging a Purkinje system of the heart of the patient.

27. A system comprising:
electrode apparatus comprising a plurality of external electrodes to monitor electrical activity from tissue of a patient; and
computing apparatus comprising processing circuitry and coupled to the electrode apparatus and configured to:
monitor electrical activity using the plurality of external electrodes during delivery of ventricle from atrium (VfA) pacing therapy;
generate electrical heterogeneity information (EHI) during delivery of VfA pacing therapy;
determine whether a VfA paced setting for the VfA pacing therapy is acceptable based on the EHI generated from the electrical activity using the VfA paced setting; and
adjust the paced setting for the VfA pacing therapy based on whether the VfA pacing therapy is acceptable.

* * * * *